(12) United States Patent
Silverman et al.

(10) Patent No.: US 8,603,782 B2
(45) Date of Patent: Dec. 10, 2013

(54) HEAT LYSIS PRODUCTION OF PROTEINS

(75) Inventors: Joshua Silverman, Sunnyvale, CA (US); Wayne To, Fremont, CA (US)

(73) Assignee: Amgen Inc., Thousand Oaks, CA (US)

(*) Notice: Subject to any disclaimer, the term of this patent is extended or adjusted under 35 U.S.C. 154(b) by 1518 days.

(21) Appl. No.: 11/457,080

(22) Filed: Jul. 12, 2006

(65) Prior Publication Data

US 2008/0003611 A1 Jan. 3, 2008

Related U.S. Application Data

(60) Provisional application No. 60/699,137, filed on Jul. 13, 2005.

(51) Int. Cl.
C07K 1/00 (2006.01)
C12N 15/74 (2006.01)

(52) U.S. Cl.
USPC .......................................... 435/71.2; 530/427

(58) Field of Classification Search
None
See application file for complete search history.

(56) References Cited

U.S. PATENT DOCUMENTS

| | | | |
|---|---|---|---|
| 5,663,143 A * | 9/1997 | Ley et al. | 514/12 |
| 6,057,287 A * | 5/2000 | Markland et al. | 514/2 |
| 6,333,402 B1 * | 12/2001 | Markland et al. | 536/23.5 |
| 7,413,537 B2 * | 8/2008 | Ladner et al. | 506/14 |
| 7,413,877 B2 * | 8/2008 | Collier et al. | 435/71.1 |
| 2004/0209243 A1 * | 10/2004 | Nixon et al. | 435/5 |
| 2005/0048512 A1 * | 3/2005 | Kolkman et al. | 435/6 |
| 2005/0089932 A1 | 4/2005 | Kolkman et al. | |
| 2005/0136049 A1 * | 6/2005 | Ledbetter et al. | 424/132.1 |
| 2005/0164301 A1 | 7/2005 | Kolkman et al. | |
| 2006/0008844 A1 * | 1/2006 | Stemmer et al. | 435/7.1 |
| 2006/0177831 A1 | 8/2006 | Stemmer et al. | |
| 2006/0223114 A1 | 10/2006 | Stemmer et al. | |
| 2006/0234299 A1 | 10/2006 | Stemmer et al. | |
| 2008/0281076 A1 | 11/2008 | Bakker et al. | |

FOREIGN PATENT DOCUMENTS

WO WO 2004/044011 A2 * 5/2004

OTHER PUBLICATIONS

Perry, L.J. and Wetzel, R., 1984, "Disulfide bond engineered into T4 lysozyme: Stabilization of the protein toward thermal inactivation", Science, vol. 226, No. 4674, pp. 555-557.*
Pantoliano, M.W., et al., 1987, "Protein engineering of subtilisin BPN': Enhanced stabilization through the introduction of two cysteines to form a disulfide bond", vol. 26, pp. 2077-2082.*
Creighton, T.E., 1988, "Disulfide bonds and protein stability", BioEssays, vol. 8, No. 2, pp. 57-63.*
Matsumura, M., et al., 1989, "Stabilization of phage T4 lysozyme by engineered disulfide bonds", Proceedings of the National Academy of Sciences, U.S.A., vol. 86, pp. 6562-6566.*
Simmons, T., et al., 1997, "Human low density lipoprotein receptor fragment. Successful refolding of a functionally active ligand-binding domain produced in *Escherichia coli*", The Journal of Biological Chemistry, vol. 272, No. 41, pp. 25531-25536.*
Rong, L., et al., 1998, "Conversion of a human low density lipoprotein receptor ligand-binding repeat to a virus receptor: Identification of residues important for ligand specificity", Proceedings of the National Academy of Sciences, U.S.A., vol. 95, No. 15, pp. 8467-8472.*
Kirk, N., and Cowan, D., 1995, "Optimising the recovery of recombinant thermostable proteins expressed in mesophilic hosts", Journal of Biotechnology, vol. 42, No. 2, pp. 177-184.*
Soskic, V., et al., 1997, "A simple procedure for the preparation of *Thermus* flavus DNA polymerase", Yugoslovenska Medicinska Biokemija, vol. 16, No. 3, pp. 143-146.*
Kim. R., et al., 1998, Proceedings of the National Academy of Sciences, USA, vol. 95, No. 16, pp. 9129-9133.*
Joe, M. H., et al., 2000, Molecules and Cells, vol. 10, No. 5, pp. 519-524.*
Simmons, T., et al., 1997, "Human Low Density Lipoprotein Receptor Fragment", The Journal of Biological Chemistry, vol. 272, No. 41, pp. 25531-25536.*
Korn et al, Recombinant bispecific antibodies for the targeting of adenoviruses to CEA-expressing tumour cells: a comparative analysis of bacterially expressed single-chain diabody and tandem scFv, J Gene Med, 2004, pp. 642-651.
Kalthoff, A novel strategy for the purification of recombinantly expressed unstructured protein domains, J Chromatogr B analyt Technol Biomed Life Sci, Mar. 2003, 786(1-2), pp. 247-254.
Lee et al., Identification and distribution of protein families in 120 completed genomes using Gene3D, Proteins, May 15, 2005; 59(3), pp. 603-615.
LeGall et al., Effect of linker sequences between the antibody variable domains on the formation, stability and biological activity of a bispecific tandem diabody, Protein Eng Des Sci, Apr. 2004; 17(4), pp. 357-366.
Letunic, et al., SMART 5: domains in the context of genomes and networks, Nucleic Acids Res, 2006, V. 34 (database issue): D257-60.
Pearl et al., The CATH domain structure database and related resources Gene3D and DHS provide comprehensive domain family information for genome analysis, Nucleic Acids Res., 2005, V. 33 (database issue):D247-251.
Zhu, et al., A continuous thermal lysis procedure for the large-scale preparation of plasmid DNA, J Biotechnol, Aug. 2005, 118(3), pp. 257-264.

\* cited by examiner

*Primary Examiner* — Manjunath Rao
*Assistant Examiner* — William W Moore
(74) *Attorney, Agent, or Firm* — Charles Sholtz

(57) ABSTRACT

The present invention provides methods of producing isolated heat stable polypeptides by expressing the polypeptides in a prokaryotic host cell and subjecting the host cell to heat lysis. The invention further provides screening methods by producing a plurality of isolated heat stable polypeptides by expressing each of the plurality of polypeptides in a prokaryotic host cell and subjecting the host to heat lysis.

13 Claims, 5 Drawing Sheets

*Figure 2*

| | 65°C | | 75°C | | | 85°C | | | 95°C | | |
|---|---|---|---|---|---|---|---|---|---|---|---|
| | 20 min | 40 min | 20 min | 40 min | 5 min | 10 min | 20 min | 40 min | 5 min | 10 min | 40 min |
| Clone 1 | 86% | 92% | 30% | 59% | 67% | 73% | 52% | 74% | 100% | 61% | 96% |
| Clone 2 | 50% | 62% | 45% | 50% | 49% | 51% | 48% | 28% | 100% | 54% | 73% |

HEAT LYSIS PRODUCTION OF PROTEINS

CROSS-REFERENCES TO RELATED APPLICATIONS

The present application claims benefit of priority to U.S. Provisional Patent Application No. 60/699,137, filed on Jul. 13, 2005, which is incorporated by reference for all purposes.

FIELD OF THE INVENTION

The present invention relates to the production of substantially purified heat stable polypeptides by expressing the polypeptides in a prokaryotic host cell and then subjecting the host cell to heat lysis.

BACKGROUND OF THE INVENTION

Multimeric proteins comprising two or more structured cysteine loop-defined domains have therapeutic use in their ability to bind to a target molecule, for example, to initiate a cell signaling cascade, to block the interaction of an cognate receptor-ligand pair, or to target a pharmacological moiety. The design and use of numerous examples of such multimeric polypeptides have been described, including multimeric polypeptides that specifically bind to interleukins (e.g., IL-6), intracellular signaling cascade proteins (e.g., c-MET kinase), cell surface receptors (e.g., CD40) and cell surface adhesion molecules (i.e., integrins) (e.g., VLA-4), and cell surface co-stimulatory molecules (e.g., ICOS). See, for example, U.S. Patent Publication Nos.: 2003/0082630; 2003/0157561; 2005/0048512; 2005/0053973; 2005/0089932; 2005/0164301; 2006/0008844 and co-pending U.S. patent application Ser. Nos. 11/281,245 and 11/281,256, the disclosures of each of which are hereby incorporated herein by reference in their entirety for all purposes.

An important characteristic of the discrete monomer domains of these multimeric proteins includes their ability to fold independently of the other domains in the same protein. Folding of these domains may require limited assistance from, e.g., a chaperonin(s) (e.g., a receptor-associated protein (RAP)), a metal ion(s), or a co-factor. The ability to fold independently prevents misfolding of the domain when it is inserted into a new protein or a new environment, and contributes to heat stability of the individual domains as well as the full-length protein.

Proteins that contain these domains are involved in a variety of processes, such as cellular transporters, cholesterol movement, signal transduction and signaling functions which are involved in development and neurotransmission. See, Herz, (2001) *Trends in Neurosciences* 24(4):193-195; Goldstein and Brown, (2001) *Science* 292: 1310-1312. The function of a discrete monomer domain is often specific but it also contributes to the overall activity of the protein or polypeptide. For example, the LDL-receptor class A domain (also referred to as a class A module, a complement type repeat or an A-domain) is involved in ligand binding while the gamma-carboxyglumatic acid (Gla) domain which is found in the vitamin-K-dependent blood coagulation proteins is involved in high-affinity binding to phospholipid membranes. Other discrete monomer domains include, e.g., the epidermal growth factor (EGF)-like domain in tissue-type plasminogen activator which mediates binding to liver cells and thereby regulates the clearance of this fibrinolytic enzyme from the circulation and the cytoplasmic tail of the LDL-receptor which is involved in receptor-mediated endocytosis.

It is advantageous to develop methods for efficiently and cost-effectively producing multimeric proteins having two or more cysteine-defined loop domains, especially processes that are amenable to large-scale production. The present invention addresses this and other needs.

BRIEF SUMMARY OF THE INVENTION

The present invention provides methods for producing isolated heat stable synthetic polypeptides. In some embodiments, the heat stable synthetic polypeptides comprise at least two domains, wherein each domain comprises at least two disulfide bonds and is at least 25 amino acids long. In one embodiment, the methods comprise:
  culturing prokaryote cells that recombinantly express the polypeptide;
  heating the cells to between 50-100° C. for a time sufficient to lyse at least 50% of the cells; and
  separating the expressed polypeptide from intact cells and lysed cells, thereby producing an isolated heat stable synthetic polypeptide.

In another aspect, the invention provides methods for identifying a heat stable synthetic polypeptide that binds to a target molecule. In one embodiment, the methods comprise:
  growing a plurality of different cultures of prokaryote cells, wherein the different cultures recombinantly express a different heat stable polypeptide comprising at least two domains, wherein each domain comprises at least two disulfide bonds and is at least 25 amino acids long;
  heating the cells to between 50-100° C. for time sufficient to lyse at least 50% of the cells;
  separating the expressed polypeptides from intact cells and lysed cells, thereby producing isolated heat stable synthetic polypeptides; and
  screening the isolated polypeptides for a desired function, whereby the isolated heat stable synthetic polypeptide that has a desired function is identified.

With regard to the embodiments for both the production and screening (i.e., identification) methods, in some embodiments, the heating step comprises heating the cells to 65-95° C. for a time sufficient to lyse at least 50% of the cells.

In some embodiments, the polypeptide comprises at least three domains, wherein each domain comprises at least two disulfide bonds.

In some embodiments, each domain is between 25-100 amino acids long.

In some embodiments, the polypeptide has no more than 6 domains.

In some embodiments, the polypeptide has no more than 300 amino acids.

In some embodiments, each domain comprises at least three disulfide bonds.

In some embodiments, the polypeptides are expressed in the cytoplasm.

With regard to the embodiments for the screening methods, in some embodiments, the desired function is the ability to bind to a target molecule.

In some embodiments, the plurality of cultures are cultured and/or heated in one or more multi-well containers.

In some embodiments, the screening step is performed in one or more multi-well containers.

DEFINITIONS

The terms "domain," "monomer domain" or "monomer" are used interchangeably and herein refer to a discrete region found in a protein or polypeptide. A monomer domain forms a three-dimensional structure in solution in the absence of flanking amino acid sequences. Monomer domains of the invention will often bind to a target molecule. As used herein, the term "monomer domain" does not encompass the complementarity determining region (CDR) or variable region of an antibody.

The term "loop" refers to that portion of a monomer domain that is typically exposed to the environment by the assembly of the scaffold structure of the monomer domain protein, and which is involved in target binding. The present invention provides three types of loops that are identified by specific features, such as, potential for disulfide bonding, bridging between secondary protein structures, and molecular dynamics (i.e., flexibility).

As used herein, the term "cysteine-defined loop sequence" refers to a subsequence of a naturally occurring monomer domain-encoding sequence that is bound at each end by a cysteine residue that is conserved with respect to at least one other naturally occurring monomer domain of the same family. Cysteine-defined loop sequences are identified by multiple sequence alignment of the naturally occurring monomer domains, followed by sequence analysis to identify conserved cysteine residues. The sequence between each consecutive pair of conserved cysteine residues is a cysteine-defined loop sequence. The cysteine-defined loop sequence does not include the cysteine residues adjacent to each terminus. Monomer domains having cysteine-defined loop sequences include the LDL receptor A-domains, EGF-like domains, thrombospondin domains, thyroglobulin domains, trefoil/PD domains, Notch/LNR monomer domains, DSL monomer domains, Anato monomer domains, integrin beta monomer domains, Ca-EGF monomer domains, and the like.

Thus, for example, in the case of LDL receptor A-domains represented by the consensus sequence, $CX_6CX_4CX_6CX_5CX_8C$, wherein $X_6$, $X_4$, $X_5$, and $X_8$ each represent a cysteine-defined loop sequence comprising the designated number of amino acids. The thrombospondin domains are represented by the consensus sequence, $CX_3CX_{10}CX_{16}CX_{11}CX_4C$, wherein $X_3$, $X_{10}$, $X_{16}$, $X_{11}$, and $X_4$, each represent a cysteine-defined loop sequence; trefoil/PD domains are represented by the consensus sequence, $CX_{10}CX_9CX_4CCX_{10}C$, wherein $X_{10}$, $X_9$, $X_4$, and $X_{10}$, each represent a cysteine-defined loop sequence; and thyroglobulin domains are represented by the consensus sequence, $CX_{26}CX_{10}CX_6CX_1CX_{18}C$, wherein $X_{26}$, $X_{10}$, $X_6$, $X_1$, and $X_{18}$, each represent a cysteine-defined loop sequence. Notch/LNR monomer domains are represented by the consensus sequence, $CX_7CX_8CX_3CX_4CX_6C$, wherein $X_7$, $X_8$, $X_3$, $X_4$, and $X_6$ each represent a cysteine-defined loop sequence; DSL monomer domains are represented by the consensus sequence, $CX_8CX_3CX_{11}CX_7CX_8C$, wherein $X_8$, $X_3$, $X_{11}$, $X_7$, and $X_8$ each represent a cysteine-defined loop sequence; Anato monomer domains are represented by the consensus sequence, $CCX_{12}CX_{12}CX_6CC$ wherein $X_{12}$, $X_{12}$, and $X_6$ each represent a cysteine-defined loop sequence; integrin beta monomer domains are represented by the consensus sequence, $CX_2CX_6CX_2CX_{15}CX_{10}C$, wherein $X_2$, $X_6$, $X_2$, $X_{15}$, and $X_{10}$ each represent a cysteine-defined loop sequence; and Ca-EGF monomer domains are represented by the consensus sequence, $CX_6CX_6CX_8CX_2CX_{13}C$, wherein $X_6$, $X_6$, $X_8$, $X_2$, and $X_{13}$ each represent a cysteine-defined loop sequence.

The term "multimer" is used herein to indicate a polypeptide comprising at least two monomer domains. The separate monomer domains in a multimer can be joined together by a linker.

The terms "target molecule" or "target" interchangeably encompass a wide variety of substances and molecules, which range from simple molecules to complex targets. Target molecules can be proteins, nucleic acids, lipids, carbohydrates or any other molecule capable of recognition by a polypeptide domain. For example, a target molecule can include a chemical compound (i.e., non-biological compound such as, e.g., an organic molecule, an inorganic molecule, or a molecule having both organic and inorganic atoms, but excluding polynucleotides and proteins), a mixture of chemical compounds, an array of spatially localized compounds, a biological macromolecule, a bacteriophage peptide display library, a polysome peptide display library, an extract made from a biological materials such as bacteria, plants, fungi, or animal (e.g., mammalian) cells or tissue, a protein, a toxin, a peptide hormone, a cell, a virus, or the like. Other target molecules include, e.g., a whole cell, a whole tissue, a mixture of related or unrelated proteins, a mixture of viruses or bacterial strains or the like. Target molecules can also be defined by inclusion in screening assays described herein or by enhancing or inhibiting a specific protein interaction (i.e., an agent that selectively inhibits a binding interaction between two predetermined polypeptides). As used herein, the terms "target molecule" or "target" do not include a CDR or variable region of an antibody.

The term "linker" is used herein to indicate a moiety or group of moieties that joins or connects two or more discrete separate monomer domains. The linker allows the discrete separate monomer domains to remain separate when joined together in a multimer. The linker moiety is typically a substantially linear moiety. Suitable linkers include polypeptides, polynucleic acids, peptide nucleic acids and the like. Suitable linkers also include optionally substituted alkylene moieties that have one or more oxygen atoms incorporated in the carbon backbone. Typically, the molecular weight of the linker is less than about 2000 daltons. More typically, the molecular weight of the linker is less than about 1500 daltons and usually is less than about 1000 daltons. The linker can be small enough to allow the discrete separate monomer domains to cooperate, e.g., where each of the discrete separate monomer domains in a multimer binds to the same target molecule via separate binding sites. Exemplary linkers include a polynucleotide encoding a polypeptide, or a polypeptide of amino acids or other non-naturally occurring moieties. The linker can be a portion of a native sequence, a variant thereof, or a synthetic sequence. Linkers can comprise, e.g., naturally occurring, non-naturally occurring amino acids, or a combination of both.

The terms "polypeptide," "peptide," and "protein" are used herein interchangeably to refer to an amino acid sequence of two or more amino acids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

"Conservative amino acid substitution" refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "synthetic" refers to a polypeptide that is non-naturally occurring, i.e., whose sequence has been manipulated by man. Synthetic polypeptides can be produced using non-biological (i.e., using a synthesizer) or biological systems (i.e., recombinantly produced). For example, in some embodiments, the synthetic polypeptides isolated by the present methods can be a member of a library of synthetic polypeptides, wherein each polypeptide member has consistent amino acid residues at positions correlating with conserved residues in domain consensus sequences and variable amino acid residues at positions correlating with non-conserved residues in domain sequences. In some embodiments, the synthetic polypeptides share less than 95% sequence identity with any known naturally occurring sequence that can be retrieved in a gene database, for example, less than 95% sequence identity using BLAST to search GenBank.

The phrase "nucleic acid sequence" refers to a single or double-stranded polymer of deoxyribonucleotide or ribonucleotide bases or an analog thereof.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription that are involved in recognition and binding of RNA polymerase and other proteins to initiate transcription.

A "vector" refers to a polynucleotide, which when independent of the host chromosome, is capable of replication in a host organism. Examples of vectors include plasmids. Vectors typically have an origin of replication. Vectors can comprise, e.g., transcription and translation terminators, transcription and translation initiation sequences, and promoters useful for regulation of the expression of the particular nucleic acid.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The phrase "specifically (or selectively) binds" refers to a binding reaction that can be determinative of the presence of the polypeptide in a heterogeneous population of proteins (e.g., a cell or tissue lysate) and other biologics. Thus, under standard conditions or assays used in antibody binding assays, the specified monomer or multimer binds to a particular target molecule above background (e.g., 2×, 5×, 10× or more above background) and does not bind in a significant amount to other molecules present in the sample.

The terms "identical" or percent "identity," in the context of two or more nucleic acid sequences or amino acid sequences, refer to two or more sequences or subsequences that are the same. "Substantially identical" refers to two or more nucleic acids or polypeptide sequences having a specified percentage of amino acid residues or nucleotides that are the same (i.e., 70%, 75%, 80%, 85%, 90%, 95%, 96%, 97%, 98% or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity or substantial identity exists over a region that is at least about 10 to 50 nucleotides or amino acids in length, or more preferably over a region that is 50 to 100 or 300 or more nucleotides or amino acids in length.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is the BLAST 2.0 algorithm, which is described in Altschul et al. (1990) J. Mol. Biol. 215:403-410, respectively. Software for performing BLAST analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "heat stable" refers to the ability of a polypeptide to retain solubility and functionality upon exposure for ≥10 minutes at ≥55° C. A heat stable polypeptide, when heated at ≥55° C. for ≥10 minutes, retains significant function and does not substantially precipitate out of solution. By "substantially precipitate out of solution" is meant at least 90% of the heat treated protein remains soluble. Functionality can be measured according to assays known in the art to measure the functionality of a polypeptide of interest. In some embodiments, functionality is measured by the ability of the heat stable polypeptide to specifically bind to a target molecule, using techniques well known in the art (e.g., standard binding assays including solid-phase radioimmunoassay, ELISA, and the like. See, for example, Harlow and Lane, *Using Antibodies,* 1998, Cold Spring Harbor Laboratory Press).

As used herein, the term "isolated" refers to the substantial separation or substantial purification of a heat stable polypeptide of interest from other cellular components of the prokaryotic host cell. For example, an isolated heat stable polypeptide is at least about 70% purified from the other cellular components of the prokaryotic host cell.

BRIEF DESCRIPTION OF THE DRAWINGS

FIG. 2 illustrates that protein recovery of heat stable proteins using heat lysis is efficient over a broad temperature range. Clone 1=trimer; Clone 2=monomer.

DETAILED DESCRIPTION

1. Introduction

Figure 1:
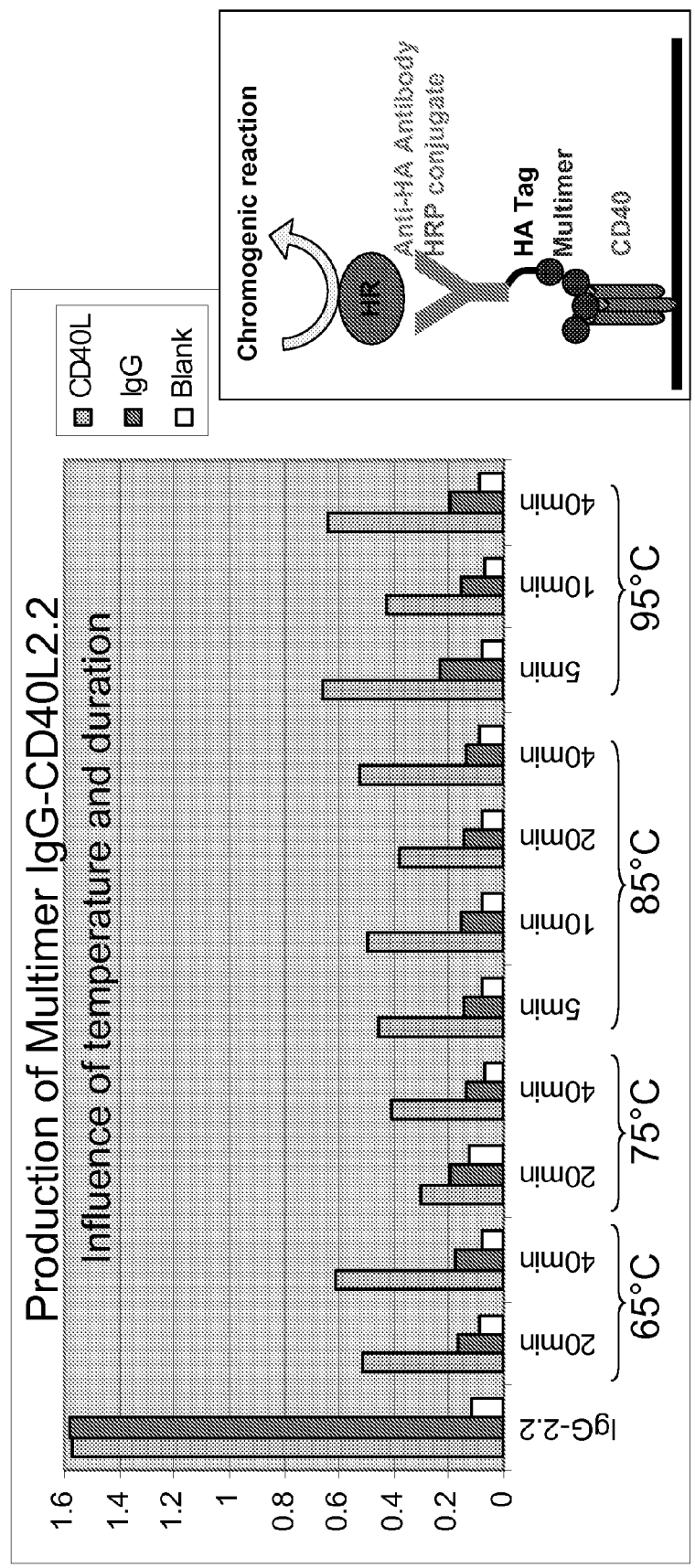
FIG. 1 illustrates the influence of temperature and time on the functionality of multimer IgG-CD40L2.2. Heat treatment conditions did not influence the functionality of multimer IgG-CD40L2.2 to specifically bind to its ligand.

The present invention provides methods for the efficient and cost effective production of isolated heat stable multimeric polypeptides having two or more cysteine-defined loop domains, by subjecting the prokaryotic host cells in which the polypeptide is exposed to heat lysis, i.e., exposed to a temperature of at least about 65° C. for a time sufficient to lyse at least about 50% of the cells.

The majority of bacterial proteins irreversibly denature and precipitate when exposed to heat. Others have described subjecting unstructured polypeptide chains expressed in bacteria and plasmid DNA to heat lysis as part of scaleable pre-purification processes. See, Kalthoff, *J Chromatogr B Analyt Technol Biomed Life Sci* (2003) 786:247-54; and Zhu, et al., *J Biotechnol* (2005) 118:257-64. However, the heat lysis process was not applied to polypeptides that form a particular structure associated with a functionality. Furthermore, the instability of multimeric structured polypeptides, for example immunoglobulin domains, has been reported. See, Korn, et al., *J Gene Med* (2004) 6:642-51; and Le Gall, et al., *Protein Eng Des Sel* (2004) 17:357-66. Surprisingly, the heat stable multimeric polypeptides of the present invention have multiple structured domains that nevertheless remain stable upon exposure to heat, and therefore can be efficiently isolated from other prokaryotic proteins upon heat lysis of the host cells.

2. Production Methods a. Heat Stable Polypeptides

Generally, the heat stable polypeptides used in the present methods are comprised of at least 2 structured domains, and can have up to 15 domains, for example, 3, 4, 5, 6, 7, 8, 9, 10, 11, 12, 13, 14 or 15 domains. The individual domain monomers can be the same ("homo-multimer") or different ("hetero-multimer"). Each domain has at least two disulfide bonds, and can have three, four, five, or more disulfide bonds, thereby imparting structure to each domain. Monomer domains are typically heat stable in isolation or as part of a larger multimer. Each domain can have from about 25 to about 500 amino acids in length, for example, about 25-500, 25-200, 25-100, 25-60, 30-100, 50-150, 40-90 or 50-80 amino acids, for example, about 25, 30, 35, 40, 45, 50, 55, 60, 65, 70, 75, 80, 85, 90, 100, 150, 200, 300, 400, 500 amino acids in length. Accordingly, the heat stable polypeptides used in the present methods can have a total length of from about 50 to about 5000 amino acids, for example about 50-5000, 60-1000, 60-300, 60-400, 60-500, 75-800, 90-600 in length, for example, about 50, 60, 75, 90, 100, 200, 300, 400, 500, 600, 700, 800, 900, 1000, 1100, 1200, 1300, 1400, 1500, 2000, 3000 or 5000 total amino acids in length.

Exemplary monomer domains that are particularly suitable for use in the practice of the present invention are cysteine-rich domains comprising disulfide bonds. Typically, the disulfide bonds promote folding of the domain into a three-dimensional structure. Usually, cysteine-rich domains have at least two disulfide bonds, more typically at least three disulfide bonds. Suitable cysteine rich monomer domains include without limitation, e.g., LDL receptor A-domains, EGF-like domains, thrombospondin type 1 domains, trefoil domains, thyroglobulin domains, Notch/LNR domains, DSL domains, Anato domains, integrin beta domains, Ca-EGF domains, SHKT domains, Conotoxin domains, Defensin beta domains, Defensin 2 (arthropod) domains, Defensin 1 (mammalian) domains, toxin 2 (scorpion short) domains, toxin 3 (scorpion) domains, toxin 4 (anemone) domains, toxin 12 (spider) domains, Mu conotoxin domains, Conotoxin 11 domains, Omega Atracotoxin domains, myotoxin domains, CART domains, Fn1 domains, Fn2 domains, Delta Atracotoxin domains, toxin 1 (snake) domains, toxin 5 (scorpion short) domains, toxin 6 (scorpion) domains, toxin 7 (spider) domains, toxin 9 (spider) domains, gamma thionin domains, TSP2 domains, somatomedin B-like domains, follistatin N-terminal domain like domains, cystine knot-like domains, knot 1 domains, toxin 8 domains, and disintegrin domains. Exemplary domains are also described, for example, in U.S. patent application Ser. No. 11/281,245 (also PCT/US05/41639) and application Ser. No. 11/281,256 (also published as WO 2006/055689), the disclosures of each of which are hereby incorporated herein by reference in their entirety for all purposes.

The structure of the monomer domain is often conserved, although the polynucleotide sequence encoding the monomer need not be conserved. For example, domain structure may be conserved among the members of the domain family, while the domain nucleic acid sequence is not. Thus, a monomer domain can be classified according to a domain family, for example, a LDL receptor A-domain, an EGF-like domain, a thrombospondin type 1 domain, a trefoil domain, or a thyroglobulin domain according to its cysteine residues and other conserved residues, and optionally, its affinity for a metal ion (e.g., calcium).

In some embodiments, suitable monomer domains (e.g. domains with the ability to fold independently or with some limited assistance) can be selected from the families of protein domains that contain β-sandwich or β-barrel three dimensional structures as defined by such computational sequence analysis tools as Simple Modular Architecture Research Tool (SMART), available on the worldwide web at smart.embl.de/ (see, Letunic, et al., *Nucleic Acids Res.* (2006) 34:D257-60); or CATH, available on the worldwide web at biochem.ucl.ac.uk/bsm/cath/ (see, Pearl, et.al., *Nucleic Acids Res* (2005) 33:D247-51); or DomainFinder (Pearl, et al., *Protein Sci* (2002) 11:233-244).

Domains described herein employ exemplary motifs (i.e., scaffolds). Certain positions are marked with an "x," indicating that any amino acid can occupy the position. These positions can include a number of different amino acid possibilities, thereby allowing for sequence diversity and thus affinity for different target molecules. Use of brackets in motifs indicates alternate possible amino acids within a position (e.g., "[ekq]" indicates that either E, K or Q may be at that position). Use of parentheses in a motif indicates that that the positions within the parentheses may be present or absent (e.g., "([ekq])" indicates that the position is absent or either E, K, or Q may be at that position). When more than one "x" is used in parentheses (e.g., "(xx)"), each x represents a possible position. Thus "(xx)" indicates that zero, one or two amino acids may be at that position(s), where each amino acid is independently selected from any amino acid. α represents an aromatic/hydrophobic amino acid such as, e.g., W, Y, F, or L; β represents a hydrophobic amino acid such as, e.g., V, I, L, A, M, or F; χ represents a small or polar amino acid such as, e.g., G, A, S, or T; δ represents a charged amino acid such as, e.g., K, R, E, Q, or D; ε represents a small amino acid such as, e.g., V, A, S, or T; and φ represents a negatively charged amino acid such as, e.g., D, E, or N.

A-Domains

The A-domains (sometimes called "complement-type repeats" or "LDL receptor type or class A domains") typically contain about 25-65, and more generally about 30-50 amino acids. In some embodiments, the domains comprise about 35-45 amino acids and in some cases about 40 amino acids. Within the 30-50 amino acids, there are about 6 cysteine residues. Of the six cysteines, disulfide bonds typically are found between the following cysteines: C1 and C3 (i.e., first and third cysteines), C2 and C5 (i.e., second and fifth cysteines), C4 and C6 (i.e., fourth and sixth cysteines). The cysteine residues of the domain are disulfide linked to form a compact, stable, functionally independent moiety. Clusters of these repeats make up a target binding domain, and differential clustering can impart specificity with respect to the ligand binding.

Exemplary A domain sequences and consensus sequences are set forth below. One typical consensus sequence useful to identify A domains is the following: C-[VILMA]-$X_{(5)}$-C-[DNH]-$X_{(3)}$-[DENQHT]-C-$X_{(3,4)}$-[STADE]-[DEH]-[DE]-$X_{(1,5)}$-C, where the residues in brackets indicate possible residues at one position. "$X_{(\#)}$" indicates number of residues. These residues can be any amino acid residue. Parentheticals containing two numbers refers to the range of amino acids that can occupy that position (e.g., "[DE]-$X_{(1,5)}$-C" means that the amino acids DE are followed by 1, 2, 3, 4, or 5 residues, followed by C). This consensus sequence only represents the portion of the A domain beginning at the third cysteine. A second consensus is as follows: C-$X_{(3-15)}$-C-$X_{(4-15)}$-C-$X_{(6-7)}$-C-[N,D]-$X_{(3)}$-[D,E,N,Q,H,S,T]-C-$X_{(4-6)}$-D-E-$X_{(2-8)}$-C. The second consensus predicts amino acid residues spanning all six cysteine residues. In some embodiments, A domain variants comprise sequences substantially identical to any of the above-described sequences. Note that reference to "LDL receptor class A" domain, for the purposes of this invention, is not intended to indicate origin or binding properties of the domain.

Additional exemplary A domains include the following sequence:

$C_a X_{3-15} C_b X_{3-15} C_c X_{6-7} C_d (D,N) X_4 C_e X_{4-6} DEX_{2-8} C_f$ wherein C is cysteine, $X_{n-m}$ represents between n and m number of independently selected amino acids, and (D,N) indicates that the position can be either D or N; and wherein $C_a$-$C_e$, $C_b$-$C_e$ and $C_d$-$C_f$ form disulfide bonds.

Exemplary proteins containing naturally-occurring A-domains include, e.g., complement components (e.g., C6, C7, C8, C9, and Factor I), serine proteases (e.g., enteropeptidase, matriptase, and corin), transmembrane proteins (e.g., ST7, LRP3, LRP5 and LRP6) and endocytic receptors (e.g., Sortilin-related receptor, LDL-receptor, VLDLR, LRP1, LRP2, and ApoER2). A domains and A domain variants can be readily employed in the practice of the present invention as monomer domains and variants thereof. Further description of A domains can be found, for example, in U.S. Patent Publication Nos. 2003/0082630; 2003/0157561; 2005/0048512; 2005/0053973; 2005/0089932; 2005/0164301; 2006/0008844, the disclosures of each of which are hereby incorporated herein by reference in their entirety for all purposes.

EGF-Domains

Exemplary EGF monomer domains include the sequence:
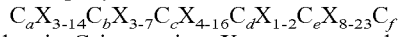
wherein C is cysteine, $X_{n-m}$ represents between n and m number of independently selected amino acids; and wherein $C_a$-$C_c$, $C_b$-$C_e$ and $C_d$-$C_f$ form disulfide bonds.

Another exemplary monomer domain that can be used in the present invention is a laminin-EGF domain. Laminin-EGF domains are typically about 30-85 or 30-80 amino acids. In some embodiments, the domains comprise about 45-65 amino acids and in some cases about 50 amino acids. Within the 45-65 amino acids, there are typically about 8 cysteine residues which interact to form 4 disulfide bonds. Laminins are a major noncollagenous component of basement membranes that mediate cell adhesion, growth migration, and differentiation. They are composed of distinct but related alpha, beta, and gamma chains. The three chains form a cross-shaped molecule that consist of a long arm and three short globular arms. The long arm consist of a coiled coil structure contributed by all three chains and cross-linked by interchain disulfide bonds.

Exemplary laminin EGF domain sequences and consensus sequences are as follows:

(1) $C_1xC_2xxxxxxx(xxx)xxC_3xxx(xxxxxx)xxxxC_4xC_5xxxxxx$
    $xxC_6xxC_7xxxxxxx(xxxxx)xxxxxxC_8$ (2) $C_1xC_2xxxxxxx(xxx)xxC_3xxx(xxxxxx)xxgxC_4xC_5xxxxxG$
    $xxC_6xxC_7xxxxxxx(xxxxx)xxxxxxC_8$ (3) $C_1xC_2[ndh]xxxxx(xxx)xxC_3xxx(xxxxxx)xxgxC_4xC_5xx$
    $xxxGxxC_6[denq]xC_7xx[gn][yfht]xxx(xxxxx)xxxxxC_8$ Ca-EGF domains contain about 30-50 or 30-65 amino acids. In some embodiments, the domains comprise about 35-60 amino acids and in some cases about 55 amino acids. Within the 35-55 amino acids, there are typically about 4 to about 6 cysteine residues. Of the six cysteines, disulfide bonds typically are found between the following cysteines: C1 and C5, C2 and C4, C3 and C6. Clusters of these repeats make up a ligand binding domain, and differential clustering can impart specificity with respect to the ligand binding.

Exemplary Ca-EGF domain sequences and consensus sequences are as follows:

(1) $C_1xx(xx)xxxxC_2x(xx)xxxxxC_3xxxxxxxxxC_4x(xxx)xC_5$
    $xxxxxxxxxx(xxxxx)xxxC_6$ (2) $DxxEC_1xx(xx)xxxxC_2x(xx)xxxxxC_3xNxxGxxxC_4x(xxx)$
    $xC_5xxxxxxxxxx(xxxxx)xxxC_6$ (3) $DxdEC_1xx(xx)xxxxC_2x(xx)xxxxxC_3xNxxGxfxC_4x(xxx)$
    $xC_5xxgxxxxxxx(xxxxx)xxxC_6$ (4) $D[vilf][Dn]EC_1xx(xx)xxxxC_2[pdg](dx)xxxxxC_3xNxx$
    $G[sgt][fy]xC_4x(xxx)xC_5xx[Gsn][\alpha s]xxxxxx(xxxxx)xxx$
    $C_6$ (5) $D[\beta][Dn]EC_1xx(xx)xxxxC_2[pdg](dx)xxxxxC_3xNxxG$
    $[sgt][\alpha]xC_4x(xxx)xC_5xx[Gsn][\alpha s]xxxxxx(xxxxx)xxxC_6$ In some embodiments, Ca-EGF domain variants comprise sequences substantially identical to any of the above-described sequences.

To date, at least 2559 naturally occurring Ca-EGF domains have identified based on cDNA sequences. Exemplary proteins containing the naturally occurring Ca-EGF domains include, e.g., membrane-bound and extracellular proteins. Ca-EGF domains are further described in, e.g., Selander-Sunnerhagen et al., *J Biol Chem.* 267(27):19642-9 (1992).

Thrombospondin Type 1 Domains

Thrombospondin type 1 ("TSP1") domains contain about 30-50 or 30-65 amino acids. In some embodiments, the domains comprise about 35-55 amino acids and in some cases about 50 amino acids. Within the 35-55 amino acids, there are typically about 4 to about 6 cysteine residues. Of the six cysteines, disulfide bonds typically are found between the following cysteines: C1 and C5, C2 and C6, C3 and C4. The cysteine residues of the domain are disulfide linked to form a compact, stable, functionally independent moiety comprising distorted beta strands. Clusters of these repeats make up a ligand binding domain, and differential clustering can impart specificity with respect to the ligand binding.

Exemplary TSP1 domain sequences and consensus sequences are as follows:

(1) $(xxxxxx)C_1xxxC_2xxxxx(x)xxxxxC_3xxxx(xxx)xxxxxC_4$
    $xxxxxx(x)xxxC_5(x)xxxxC_6$ (2) $(wxxWxx)C_1xxxC_2xxGxx(x)xRxxxC_3xxxx(Pxx)xxxxxC_4$
    $xxxxxx(x)xxxC_5(x)xxxxC_6$ (3) $(wxxWxx)C_1sxtC_2xxGxx(x)xRxrxC_3xxxx(Pxx)xxxxxC_4$
    $xxxxxx(x)xxxC_5(x)xxxxC_6$ (4) $(WxxWxx)C_1[Stnd][Vkaq][Tsp1]C_2xx[Gq]xx(x)x[Re]$
    $x[Rktvm]xC_3[vldr]xxxx([Pq]xx)xxxxxC_4[ldae]xxxxxx$
    $(x)xxxC_5(x)xxxxC_6;$ (5) $(WxxWxx)C_1[Stnd][Vkaq][Tsp1]C_2xx[Gq]xx(x)x[Re]$
    $x[Rktvm]xC_3[vldr]xxxx([Pq]xx)xxxxxC_4[ldae]xxxxxx$
    $(x)xxxC_5(x)xxxxC_6;$
and (6) $C_1[nst][aegiklqrstv][adenpqrst]C_2[adetgs]xgx$
    $[ikqrstv]x[aqrst]x[almrtv]xC_3xxxxxxxxx(xxxxxxx)C_4$
    $xxxxxxxxx(xx)C_5xxxxC_6$ In some embodiments, thrombospondin type 1 domain variants comprise sequences substantially identical to any of the above-described sequences.

To date, at least 1677 naturally occurring thrombospondin domains have been identified based on cDNA sequences. Exemplary proteins containing the naturally occurring thrombospondin domains include, e.g., proteins in the complement pathway (e.g., properdin, C6, C7, C8A, C8B, and C9), extracellular matrix proteins (e.g., mindin, F-spondin, SCO-spondin), circumsporozoite surface protein 2, and TRAP proteins of *Plasmodium*. Thrombospondin type 1 domains are further described in, e.g., Roszmusz et al., *BBRC* 296:156 (2002); Higgins et al., *J Immunol.* 155:5777-85 (1995); Schultz-Cherry et al., *J. Biol. Chem.* 270:7304-7310 (1995); Schultz-Cherry et al., *J. Biol. Chem.* 269:26783-8 (1994); Bork, *FEBS Lett* 327:125-30 (1993); and Leung-Hagesteijn et al., *Cell* 71:289-99 (1992).

Trefoil Domains

Another exemplary monomer domain suitable for use in the practice of the present invention is the trefoil domain. Trefoil monomer domains are typically about 30-50 or 30-65 amino acids. In some embodiments, the domains comprise about 35-55 amino acids and in some cases about 45 amino acids. Within the 35-55 amino acids, there are typically about 6 cysteine residues. Of the six cysteines, disulfide bonds typically are found between the following cysteines: C1 and C5, C2 and C4, C3 and C6.

To date, at least 149 naturally occurring trefoil domains have identified based on cDNA sequences. Exemplary proteins containing naturally occurring trefoil domains include, e.g., protein pS2 (TFF1), spasmolytic peptide SP (TFF2), intestinal trefoil factor (TFF3), intestinal surcease-isomaltase, and proteins which may be involved in defense against microbial infections by protecting the epithelia (e.g., *Xenopus* xP1, xP4, integumentary mucins A.1 and C.1. Trefoil domains are further described in, e.g., Sands and Podolsky, *Annu. Rev. Physiol.* 58:253-273 (1996); Carr et al., *PNAS USA* 91:2206-2210 (1994); DeA et al., *PNAS USA* 91:1084-1088 (1994); Hoffman et al., *Trends Biochem Sci* 18:239-243 (1993).

Exemplary trefoil domain sequences and consensus sequences are as follows:

(1) $C_1$(xx)xxxxxxxxxx$C_2$xx(x)xxxxxxx$C_3$xxxx$C_4C_5$xxxxx(x)xxxxx$C_6$ (2) $C_1$(xx)xxxxxxRxx$C_2$xx(x)xxxxxxx$C_3$xxxx$C_4C_5$xxxxx(x)xxxxx$C_6$ (3) $C_1$(xx)xxxpxxRxn$C_2$gx(x)pxitxxx$C_3$xxxg$C_4C_5$fdxxx(x)xxxpw$C_6$f (4) $C_1$(xx)xxx[Pvae]xxRx[ndpm]$C_2$[Gaiy][ypfst]([de]x)[pskq]x[Ivap][Tsa]xx[qedk]$C_3$xx[krln][Gnk]$C_4C_5$[Fwy][Dnrs][sdpnte]xx(x)xxx[pki][Weash]$C_6$[Fy]

(5) $C_1$(xx)xxx[Pvae]xxRx[ndpm]$C_2$[Gaiy][ypfst]([de]x)[pskq]x[Ivap][Tsa]xx[keqd]$C_3$xx[krln][Gnk]$C_4C_5$[α][Dnrs][sdpnte]xx(x)xxx[pki][Weash]$C_6$[Fy]

(6) $C_1$([dnps])[adiklnprstv][dfilmv][adenprst][adel prv][ehklnqrs][adegknsv][kqr][fiklqrtv][dnpqs]$C_2$[agiy][flpsvy][dknpqs][adfghlp][aipv][st][aegkpqrs] [adegkpqs][deiknqt]$C_3$[adefknqrt][adegknqs][gn]$C_4C_5$ [wyfh][deinrs][adgnpst][aefgqlrstw][giknsvmq]([afm prstv][degklns][afiqstv][iknpv]w)$C_6$ Thyroglobulin Domains Another exemplary monomer domain suitable for use in the present invention is the thyroglobulin domain. Thyroglobulin monomer domains are typically about 30-85 or 30-80 amino acids. In some embodiments, the domains comprise about 35-75 amino acids and in some cases about 65 amino acids. Within the 35-75 amino acids, there are typically about 6 cysteine residues. Of the six cysteines, disulfide bonds typically are found between the following cysteines: C1 and C2, C3 and C4, C5 and C6.

To date at least 251 naturally occurring thyroglobulin domains have been identified based on cDNA sequences. The N-terminal section of Tg contains 10 repeats of a domain of about 65 amino acids which is known as the Tg type-1 repeat PUBMED:3595599, PUBMED:8797845. Exemplary proteins containing naturally occurring thyroglobulin domains include e.g., the HLA class II associated invariant chain, human pancreatic carcinoma marker proteins, nidogen (entactin), insulin-like growth factor binding proteins (IGFBP), saxiphilin, chum salmon egg cysteine proteinase inhibitor, and equistatin. The Thyr-1 and related domains belong to MEROPS proteinase inhibitor family I31, clan IX. Thyroglobulin domains are further described in, e.g., Molina et al., *Eur. J. Biochem.* 240:125-133 (1996); Guncar et al., *EMBO J.* 18:793-803 (1999); Chong and Speicher, *DW* 276:5804-5813 (2001).

Exemplary thyroglobulin domain sequences and consensus sequences are as follows:

(1) $C_1$xxxxxxxxxxxxxxx(xxxxxxxxxx)xxxxxxxxxxx$C_2$xxxx xxxxxx$C_3$x(x)x(xxx)xxxx$C_4$x$C_5$xxxx(x)xxxxxxxxxxxxxx(x x)x$C_6$ (2) $C_1$xxxxxxxxxxxxxxx(xxxxxxxxxx)xxxxxxxyxPx$C_2$xxxG xxxxxQ$C_3$x(x)x(xxx)xxxx$C_4$W$C_5$Vxxx(x)Gxxxx Gxxxxxxxxx(x x)x$C_6$ (3) $C_1$xxxxxxxxxxxxxxx(xxxxxxxxxx)xxxxxxxyxPx$C_2$xxxG xyxxxQ$C_3$x(x)s(xxx)xxgx$C_4$W$C_5$Vdxx(x)Gxxxx Gxxxxxgxx(x x)x$C_6$ (4) $C_1$[qerl]xxxxxxxxxxxxxx(xxxxxxxxxx)xxxxxxx[Yfh p]xPx$C_2$xxxGx[Yf]xx[vkrl]Q$C_3$x(x[sa]xxx)xx[Gsa]x$C_4$[W yf]$C_5$V[Dnyfl]xx(x)Gxxxx[Gdne]xxxxxgxx(xx)x$C_6$ (5) $C_1$[qerl]xxxxxxxxxxxxxx(xxxxxxxxxx)xxxxxxx[αhp] xPx$C_2$xxxGx[α]xx[vkrl]Q$C_3$x(x[sa]xxx)xx[gas]x$C_4$[α]$C_5$ V[Dnα]xx(x)Gxxxx[φg]xxxxxgxx(xx)x$C_6$ Notch Domains Notch/LNR domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C5, C2 and C4, C3 and C6. Clusters of these repeats make up a ligand binding domain, and differential clustering can impart specificity with respect to the ligand binding.

Exemplary Notch/LNR domain sequences and consensus sequences are as follows:

(1) $C_1xx(xx)xxxC_2xxxxxxxxxC_3xxxC_4xxxxC_5xxxxxxxC_6$ (2) $C_1xx(xx)xxxC_2xxxxxxxxxC_3xxxC_4xxxxC_5xxDGxDC_6$ (3) $C_1xx(xx)xxxC_2xxxxxnGxC_3xxxC_4nxxxC_5xxDGxDC_6$ (4) $C_1xx(x[yiflv])xxxC_2x[dens]xxx[Nde][Gk]xC_3[nd]x$
[densa]$C_4$[Nsde]xx[aeg]$C_5$x[wyf]DGxD$C_6$ (5) $C_1xx(x[\beta\ \alpha])xxxC_2x[\phi s]xxx[\phi][Gk]xC_3[nd]x[\phi sa]$
$C_4[\phi s]xx[aeg]C_5x[\alpha]DGxDC_6$ (6) $C_1xxxx(xx[hy])C_2[agdkqw][adeklrsv][dhklrswy][a$
firy][aghknrs][dn][gknqs][fhiknqrvy]$C_3$[dehns][eklq
prsy][adegq]$C_4$[dns][flnsty][aehpsy][aegk]$C_5$[degkln
q][fwy]d[gn][fglmy]d$C_6$ In some embodiments, Notch/LNR domain variants comprise sequences substantially identical to any of the above-described sequences.

To date, at least 153 naturally occurring Notch/LNR domains have identified based on cDNA sequences. Exemplary proteins containing the naturally occurring Notch/LNR domains include, e.g., transmembrane receptors. Notch/LNR domains are further described in, e.g., Sands and Podolsky Annu. Rev. Physiol. 58:253-273 (1996); Carr et al., PNAS 91:2206-2210 (1994); and DeA et al., PNAS 91:1084-1088 (1994)).

DSL Domains

DSL domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C5, C2 and C4, C3 and C6. Clusters of these repeats make up a ligand binding domain, and differential clustering can impart specificity with respect to the ligand binding.

Exemplary DSL domain sequences and consensus sequences are as follows:

(1) $C_1xxxxxxxxxC_2xxxC_3xxxxxxxxxxxxC_4xxxGxxxC_5xxxxxxx$
$xC_6$ (2) $C_1xxxYxxxxC_2xxxC_3xxxxxxxxxxxxC_4xxxGxxxC_5xxGWxGx$
$xC_6$ (3) $C_1xxxYygxxC_2xxfC_3xxxxdxxxhxxxC_4xxxGxxxC_5xxGWxGx$
$xC_6$ (4) $C_1xxx$[Ywf][Yfh][Gasn]xx$C_2$xx[Fy]$C_3$x[pae]xx[Da]x
x[glast][Hrgk][ykfw]x$C_4$[dsgn]xxGxxx$C_5$xxG[Wlfy]xGxx
$C_6$ (5) $C_1xxx[\alpha][\alpha h]$[Gsna]xx$C_2$xx[$\alpha$]$C_3$x[pae]xx[Da]xx
[$\chi$1][Hrgk][ $\alpha$k]x$C_4$[dnsg]xxGxxx$C_5$xxG[$\alpha$]xGxx$C_6$ (6) $C_1$[adns][dels][hny][wy][yfh][gns][adefpst][gkn
rst]$C_2$[adnst][dkrtv][fly]$C_3$[dkr][kp]r[dn][ade][afh
kqrst]fg[gh][fsy][artv]$C_4$[dgnqs][epqsy][dnqrsty]g -continued
[enqsv][iklr][agilstv]$C_5$[dlmn][denspt]gw[kmqst]g[k
edpq][deny]$C_6$ In some embodiments, DSL domain variants comprise sequences substantially identical to any of the above-described sequences.

To date, at least 100 naturally occurring DSL domains have identified based on cDNA sequences. Exemplary proteins containing the naturally occurring DSL domains include, e.g., lag-2 and apx-1. DSL domains are further described in, e.g., Vardar et al., Biochemistry 42:7061 ((2003)); Aster et al., Biochemistry 38:4736 (1999); Kimble et al., Annu Rev Cell Dev Biol 13:333-361 (1997); Artavanis-Tsokanas et al., Science 268:225-232 (1995); Fitzgerald et al., Development 121:4275-82 (1995); Tax et al, Nature 368:150-154 (1994); and Rebayl et al., Cell 67:687-699 (1991).

Anato Domains

Anato domains contain about 30-50 or 30-65 amino acids. In some embodiments, the domains comprise about 35-55 amino acids and in some cases about 35 or about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary anato domain sequences and consensus sequences are as follows:

(1) $C_1C_2xxxxxxxxx(x)xxxxC_3xxxxxxxxxx(xx)xxC_4xxxxxxxC_5$
$C_6$ (2) $C_1C_2xdgxxxxx(x)xxxxC_3exrxxxxxx(xx)xxC_4xxxfxxC_5C_6$ (3) $C_1C_2x$[Dhtl][Ga]xxxx[plant](xx) xxxx$C_3$[esqdat
]x[Rlps]xxxxxx([gepa]x)xx$C_4$xx[avfpt][Fqvy]xx$C_5C_6$ (4) $C_1C_2x$[adehlt]gxxxxxxxxx(x)[derst]$C_3$xxxxxxxxxx(xx
[aersv])$C_4$xx[apvt][fmq][eklqrtv][adehqrsk](x)$C_5C_6$ In some embodiments, anato domain variants comprise sequences substantially identical to any of the above-described sequences.

To date, at least 188 naturally occurring anato domains have identified based on cDNA sequences. Exemplary proteins containing the naturally occurring anato domains include, e.g., C3a, C4a and C5a anaphylatoxins. Anato domains are further described in, e.g., Pan et al., J. Cell. Biol. 123: 1269-1277 (1993); Hugli, Curr Topics Microbiol Immunol. 153:181-208 (1990); and Zuiderweg et al., Biochemistry 28:172-85 (1989)).

Integrin Beta Domains

Integrin beta domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. The cysteine residues of the domain are disulfide linked to form a compact, stable, functionally independent moiety comprising distorted beta strands. Clusters of these repeats make up a ligand binding domain, and differential clustering can impart specificity with respect to the ligand binding.

Exemplary integrin beta domain sequences and consensus sequences are as follows:

(1) C$_1$xxC$_2$xxxxxxC$_3$xxC$_4$xxxxxxxx(xx)xxxxxC$_5$xxxxxxxxx xC$_6$ (2) C$_1$xxC$_2$xxxxxxC$_3$xxC$_4$xxxxxxxx(xx)xxxxRC$_5$dxxxxLxxx xC$_6$ (3) C$_1$xxC$_2$xxxxpxC$_3$xwC$_4$xxxxfxxx(gx)xxxxRC$_5$dxxxxLxxx gC$_6$ (4) C$_1$xxC$_2$[ilv]xx[ghds][Pk]xC$_3$[agst][Wyfl]C$_4$xxxx[F ly]xxx([Gr]xx)x[sagt]xRC$_5$[Dnae]xxxxL[likv]xx[Gn]C$_6$ (5) C$_1$xxC$_2$[β]xx[ghds][Pk]xC$_3$[χ][ α]C$_4$xxxx[α]xxx ([Gr]xx)x[χ]xRC$_5$[Dnae]xxxxL[βk]xx[Gn]C$_6$ (6) C$_1$[aegkqrst][kreqd]C$_2$[il][aelqrv][vilas][dghs] [kp]xC$_3$[gast][wy]C$_4$xxxx[fl]xxxx(xxxx[vilar]r)C$_5$ [and][dilrt][iklpqrv][adeps][aenq]l[iklqv]x[adknr] [gn]C$_6$ (7) C$_1$[aegkqrst][δ]C$_2$[il][aelqrv][βs][dghs][kp]xC$_3$ [χ][wy]C$_4$xxxx[fl]xxxx(xxxx[βr]r)C$_5$[and][dilrt][ikl pqrv][adeps][aenq]l[iklqv]x[adknr][gn]C$_6$ In some embodiments, integrin beta domain variants comprise sequences substantially identical to any of the above-described sequences.

To date, at least 126 naturally occurring integrin beta domains have been identified based on cDNA sequences. Exemplary proteins containing integrin beta domains include, e.g., receptors for cell adhesion to extracellular matrix proteins. Integrin beta domains are further described in, e.g., Jannuzi et al., *Mol Biol Cell.* 15(8):3829-40 (2004); Zhao et al., *Arch Immunol Ther Exp.* 52(5):348-55 (2004); and Calderwood et al., *PNAS USA* 100(5):2272-7 (2003).

SHKT Domains

SHKT domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C6, C2 and C5, C3 and C4. Clusters of these repeats make up a ligand binding domain, and differential clustering can impart specificity with respect to the ligand binding.

Exemplary SHKT domain sequences and consensus sequences are as follows:

(1) C$_1$x(xxx)xxx(x)xxC$_2$xxxxxx(xxx)C$_3$xxxx(x)xxxxxxxx C$_4$xxxC$_5$xxC$_6$ (2) C$_1$x(dxx)Dxx(x)xxC$_2$xxxxxx(xxx)C$_3$xxxx(x)xxxxxxxx C$_4$xxtC$_5$xxC$_6$ (3) C$_1$x(dxx)Dxx(x)xxC$_2$xxxxxx(xxx)C$_3$xxxx(x)xxxxxxxx C$_4$xxtC$_5$xxC$_6$ (4) C$_1$x([Dens]xx)[Dnfl]xx(x)xxC$_2$xx[wylfi]xxx([gqn] xx)C$_3$xxxx(x)xxxx[mvlri]xxxC$_4$[parqk][krlaq][Tsal]C$_5$ [gnkrd]xC$_6$ -continued (5) C$_1$x([φs]xx)[Dnfl]xx(x)xxC$_2$xx[αi]xxx([gqn]xx)C$_3$x xxx(x)xxxx[mvlri]xxxC$_4$[parqk][krlaq][Tsal]C$_5$[gnkr d]xC$_6$ In some embodiments, SHKT domain variants comprise sequences substantially identical to any of the above-described sequences.

To date, at least 319 naturally occurring SHKT domains have identified based on cDNA sequences. Exemplary proteins containing the naturally occurring SHKT domains include, e.g., matrix metalloproteinases. SHKT domains are further described in, e.g., Pan, *Dev. Genes Evol.* 208: 259-266 (1998)).

Defensin Domains

Defensin beta domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Defensin beta domain sequences and consensus sequences are as follows:

(1) C$_1$xxxxxxC$_2$xxxxC$_3$xxxxxxxxxC$_4$xxxxxxC$_5$C$_6$ (2) C$_1$xxxxgxC$_2$xxxxC$_3$xxxxxxigxC$_4$xxxxvxC$_5$C$_6$ (3) C$_1$xxxx[Gasted][vilaf]C$_2$[vila]xxxC$_3$[prk]xxxxx [Ivla][Gaste]xC$_4$[vilf]xxx[Vila]xC$_5$C$_6$ (4) C$_1$xxxx[χed][β]C$_2$[β]xxxC$_3$[prk]xxxxx[β][xe]xC$_4$[β] xxx[β]xC$_5$C$_6$ In some embodiments, Defensin beta domain variants comprise sequences substantially identical to any of the above-described sequences.

To date, at least 68 naturally occurring Defensin beta domains have identified based on cDNA sequences. Exemplary proteins containing the naturally occurring Defensin beta domains include, e.g., membrane pore-forming toxins. Defensin beta domains are further described in, e.g., Liu et al., *Genomics* 43:316-320 (1997) and Bensch et al., *FEBS Lett* 368:331-335 (1995)

Defensin 2 (arthropod) domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C4, C2 and C5, C3 and C6. Clusters of these repeats make up a ligand binding domain, and differential clustering can impart specificity with respect to the ligand binding.

Exemplary Defensin 2 (arthropod) domain sequences and consensus sequences are as follows:

(1) C$_2$xxxC$_3$xxx(xxx)xxxxxC$_4$x(xxx)xxxC$_5$xC$_6$ (2) C$_2$xxhC$_3$xxx(xgx)xxggxC$_4$x(xxx)xxxC$_5$xC$_6$(r)

(3) C$_2$xx[Hnde]C$_3$xx[kirl](x)[Grta](x)xx[Gr][Gast] xC$_4$x(xxx)[krqn]xxC$_5$xC$_6$(r)

-continued (4) $C_2xx[Hnde]C_3xx[kirl](x)[Grta](x)xx[Gr][\chi]xC_4x$
    $(xxx)[krqn]xxC_5xC_6(r)$ In some embodiments, Defensin 2 (arthropod) domain variants comprise sequences substantially identical to any of the above-described sequences.

To date, at least 58 naturally occurring Defensin 2 (arthropod) domains have identified based on cDNA sequences. Exemplary proteins containing the naturally occurring Defensin 2 (arthropod) domains include, e.g., antibacterial peptides. Defensin 2 (arthropod) domains are further described in, e.g., Cornet et al., *Structure* 3:435-448 (1995).

Defensin 1 (mammalian) domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C5, C2 and C4, C3 and C6. Clusters of these repeats make up a ligand binding domain, and differential clustering can impart specificity with respect to the ligand binding.

Exemplary Defensin 1 (mammalian) domain sequences and consensus sequences are as follows:

(1) $C_1xC_2xxxxC_3xxxxxxxxxC_4xxxxxxxxxC_5C_6$ (2) $C_1xC_2rxxxC_3xxxerxxGxC_4xxxgxxxxxC_5C_6$ (3) $C_1xC_2[Rtk]xxxC_3xx[rtgsp][Eyd][Rlsyk]xGxC_4xxx$
    $[Gnfh][vilar]x[yfhw]x[flyr]C_5C_6[ryvk]$ (4) $C_1xC_2[Rtk]xxxC_3xx[rtgsp][Eyd][Rlsyk]xGxC_4xxx$
    $[Gnfh][\beta r]x[\alpha h]x[\alpha r]C_5C_6[ryvk]$ In some embodiments, Defensin 1 (mammalian) domain variants comprise sequences substantially identical to any of the above-described sequences.

To date, at least 53 naturally occurring Defensin 1 (mammalian) domains have identified based on cDNA sequences. Exemplary proteins containing the naturally occurring Defensin 1 (mammalian) domains include, e.g., cationic, microbicidal peptides. Defensin 1 (mammalian) domains are further described in, e.g., White et al., *Curr Opin Struct Biol* 5(4):521-7 (1995).

Toxin Domains

Conotoxin domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C4, C2 and C5, C3 and C6. Clusters of these repeats make up a ligand binding domain, and differential clustering can impart specificity with respect to the ligand binding.

Exemplary conotoxin domain sequences and consensus sequences are as follows:
(1) $C_1xxxxxxC_2(xxx)xxxxxxC_3C_4xxx(xxxx)_xC_5x(xxxx)xxC_6$ In some embodiments, conotoxin domain variants comprise sequences substantially identical to any of the above-described sequences.

To date, at least 351 naturally occurring conotoxin domains have identified based on cDNA sequences. Exemplary proteins containing the naturally occurring conotoxin domains include, e.g., omga-conotoxins and snail toxins that block calcium channels and Conotoxin domains are further described in, e.g., Gray et al, *Annu Rev Biochem* 57:665-700 (1988) and Pallaghy et al., *J Mol Biol* 234:405-420 (1993).

Toxin 2 (scorpion short) domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C4, C2 and C6, C3 and C5. Clusters of these repeats make up a ligand binding domain, and differential clustering can impart specificity with respect to the ligand binding.

Exemplary Toxin 2 (scorpion short) domain sequences and consensus sequences are as follows:

(1) $C_1xxxxxC_2xxxC_3xxxxx(x)xxxxxC_4xxxxC_5xC_6$ (2) $C_1xxxxxC_2xxxC_3kxxxx(x)xxxgkC_4xxxkC_5xC_6$ (3) $C_1xxxxxC_2xxxC_3[Kreqd]xxxx(x)xxx[Gast][Krqe]C_4$
    $[Milvfa][ngaed]x[Kreqp]C_5[krehq]C_6$ (4) $C_1xxxxxC_2xxxC_3[\delta]xxxx(x)xxx[\chi][\delta]C_4[\beta][ngaed]x$
    $[\delta p]C_5[\delta h]C_6$ In some embodiments, Toxin 2 (scorpion short) domain variants comprise
sequences substantially identical to any of the above-described sequences.

To date, at least 64 naturally occurring Toxin 2 (scorpion short) domains have identified based on cDNA sequences. Exemplary proteins containing the naturally occurring Toxin 2 (scorpion short) domains include, e.g., charybdotoxin, kaliotoxin, noxiustoxin, and iberiotoxin. Toxin 2 (scorpion short) domains are further described in, e.g., Martin et al., *Biochem J.* 304 (Pt 1):51-6 (1994) and Lippens et al., *Biochemistry* 34(1): 13-21 (1995)

Toxin 3 (scorpion) domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Toxin 3 (scorpion) domain sequences and consensus sequences are as follows:

(1) $C_1xxxxxxx(x)xxxC_2xxxC_3xx(x)xxxxxxxxC_4xxxx(xxx)$
    $xxC_5xC_6$ (2) $C_1xxxxxxx(x)xxxC_2xxxC_3xx(x)xx[ag]xxGxC_4xxxx(xxx)$
    $xxC_5xC_6$ (3) $C_1x[ypvl]x[cifvl]xx(x)xxxC_2xxxC_3xx(x)[knrq]$
    $[Gkr][Ag]xx[Gsa]xC_4xxxx(xxx)xxC_5[Wylf]C_6$ (4) $C_1x[ypvl]x[c\beta]xx(x)xxxC_2xxxC_3xx(x)[knrq][Gkr]$
    $[Ag]xx[\chi]xC_4xxxx(xxx)xxC_5[\alpha]C_6$ In some embodiments, Toxin 3 (scorpion) domain variants comprise sequences substantially identical to any of the above-described sequences.

To date, at least 214 naturally occurring Toxin 3 (scorpion) domains have identified based on cDNA sequences. Exemplary proteins containing the naturally occurring Toxin 3 (scorpion) domains include, e.g., neurotoxins and mustard trypsin inhibitor, MTI-2. Toxin 3 (scorpion) domains are further described in, e.g., Kopeyan et al., *FEBS Lett*. 261(2):

423-6 (1990); Zhou et al., *Biochem J.* 1257(2):509-17 (1989); and Gregoire and Rochat, *Toxicon.* 21(1):153-62 (1983).

Toxin 4 (anemone) domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Toxin 4 (anemone) domain sequences and consensus sequences are as follows:

(1) $C_1xC_2xxxxxxxxxxxxxxxx(xx)xxxxC_3x(xx)xxxxxxC_4xx(x)xxxxxxC_5C_6$ (2) $C_1xC_2xxdgPxxrxxxxxGxx(xx)xxxxC_3x(xx)xxgWxxC_4xx(x)xxxxxxC_5C_6$ (3) $C_1xC_2xx[Denkq][Gast]Pxx[Rk]xxx[vilamf]xGx[vilam](xx)xxxxC_3x(xx)xx[Gsat]WxxC_4xx(x)xxx[ivlam]xxC_5C_6$ (4) $C_1xC_2xx[\phi kq][\delta]Pxx[Rk]xxx[\beta]xGx[\beta](xx)xxxxC_3x(xx)xx[\chi]WxxC_4xx(x)xxx[\beta]xxC_5C_6$ In some embodiments, Toxin 4 (anemone) domain variants comprise sequences substantially identical to any of the above-described sequences.

To date, at least 23 naturally occurring Toxin 4 (anemone) domains have identified based on cDNA sequences. Exemplary proteins containing the naturally occurring Toxin 4 (anemone) domains include, e.g., calitoxin and anthopleurin. Toxin 4 (anemone) domains are further described in, e.g., Liu et al., *Toxicon* 41(7):793-801 (2003).

Toxin 12 (spider) domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Toxin 12 (spider) domain sequences and consensus sequences are as follows:

(1) $C_1xxxxxxxC_2xxxxx(x)C_3C_4(x)xxxxxC_5xxx(xxx)x(xx)xxC_6$ (2) $C_1xxxfxxC_2xxxxd(x)C_3C_4(x)xxlxC_5xxx(xxx)x(xx)xwC_6$ (3) $C_1xx[wfvilm][fwgml]xxC_2xxxxx[Dneq](x)C_3C_4(x)xx[lyfw]xC_5xxx(xxx)x(xx)x[wlyfi]C_6$ (4) $C_1xx[\alpha\beta][fwgml]xxC_2xxxxx[\phi q](x)C_3C_4(x)xx[\alpha]xC_5xxx(xxx)x(xx)x[ai]C_6$ In some embodiments, Toxin 12 (spider) domain variants comprise sequences substantially identical to any of the above-described sequences.

To date, at least 38 naturally occurring Toxin 12 (spider) domains have identified based on cDNA sequences. Exemplary proteins containing the naturally occurring Toxin 12 (spider) domains include, e.g., spider potassium channel inhibitors.

Mu conotoxin domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C4, C2 and C5, C3 and C6. Clusters of these repeats make up a ligand binding domain, and differential clustering can impart specificity with respect to the ligand binding.

Exemplary Mu conotoxin domain sequences and consensus sequences are as follows:

(1) $C_1C_2xxxxxC_3xxxxC_4xxxxC_5C_6$ (2) $C_1C_2xxpxxC_3xxrxC_4kpxxC_5C_6$ (3) $C_1C_2xxpxxC_3xxrxC_4kpxxC_5C_6$ (4) $[Rkqe]xC_1C_2xx[Pasgt][Krqe]xC_3[Krqe]x[Rkqe]xC_4[Kreq][Pasgte]x[rkqe]C_5C_6$ (5) $[\delta]xC_1C_2xx[\chi p][\delta]xC_3[\delta]x[\delta]xC_4[\delta][\chi pe]x[\delta]C_5C_6$ In some embodiments, Mu conotoxin domain variants comprise sequences substantially identical to any of the above-described sequences.

To date, at least 4 naturally occurring Mu conotoxin domains have identified based on cDNA sequences. Exemplary proteins containing the naturally occurring Mu conotoxin domains include, e.g., sodium channel inhibitors. Mu conotoxin domains are further described in, e.g., Nielsen et al., 277:27247-27255 (2002)).

Conotoxin 11 domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C4, C2 and C5, C3 and C6. Clusters of these repeats make up a ligand binding domain, and differential clustering can impart specificity with respect to the ligand binding.

Exemplary Conotoxin 11 domain sequences and consensus sequences are as follows:

(1) $C_1xxxC_2xx(x)xxC_3xxxC_4xC_5$ (2) $C_1xxxC_2x[Satg]v([Hkerqd])x[dkenq]C_3xxxC_4[iflvma]C_5xxxx[kc6stva]x[acstva]$ (3) $C_1xxxC_2x[\chi]v([\delta h])x[dkenq]C_3xxxC_4[\beta]C_5xxxx[kc6\epsilon]x[ac6\epsilon]$ In some embodiments, Conotoxin 11 domain variants comprise sequences substantially identical to any of the above-described sequences.

To date, at least 3 naturally occurring Conotoxin 11 domains have identified based on cDNA sequences. Exemplary proteins containing the naturally occurring Conotoxin 11 domains include, e.g., spasmodic peptide, tx9a. Conotoxin 11 domains are further described in, e.g., Miles et al., *J Biol. Chem.* 277(45):43033-40 (2002).

Omega atracotoxin domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C4, C2 and C5, C3 and C6. Clusters of these repeats make up a ligand binding domain, and differential clustering can impart specificity with respect to the ligand binding.

Exemplary Omega atracotoxin domain sequences and consensus sequences are as follows:

(1) $C_1xxxxxxxC_2xxxxxxC_3C_4xxxC_5xxxxxxxxxxxxxxxC_6$ (2) $C_1xPxGxPC_2PxxxxxC_3C_4xxxC_5xxxxxxxxGxxxxxC_6$ (3) $C_1xPxGxPC_2PyxxxC_3C_4sxsC_5txkxnenGnxvxrC_6d$ (4) $C_1[Ivlamf][Pasgt]x[Gasted][Qkerd][Pasgte]C_2$ [Pasgte][Yflvia]xxx$C_3C_4$xxx$C_5$x[yflviaw][Kreqd]x [Ned][Edk][Ned][Gasted][Ned]x[Vilamf]x[Rkqe]$C_6$ [Densa]

(5) $C_1[β][χρ]x[χed][δ][χpe]C_2[χpe][By]xxxC_3C_4xxxC_5x$ [αβ][δ]x[φ][Edk][φ][χed][φ]x[β]x[δ]$C_6$[φsa]

In some embodiments, Omega atracotoxin domain variants comprise sequences substantially identical to any of the above-described sequences.

To date, at least 7 naturally occurring Omega atracotoxin domains have identified based on cDNA sequences. Exemplary proteins containing the naturally occurring Omega atracotoxin domains include, e.g., insect-specific neurotoxins. Omega atracotoxin domains are further described in, e.g., Tedford et al., *J Biol Chem.* 276(28):26568-76 (2001).

Myotoxin domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Myotoxin domain sequences and consensus sequences are as follows:

(1) $C_1xxxxxxxC_2xxxxxxC_3xxxxxxxxxxxxC_4xxxxxC_5C_6$ (2) $C_1xxxxGxC_2xPxxxxC_3xPPxxxxxxxxxC_4xWxxxC_5C_6$ (3) yxr$C_1$hxxxgh$C_2$fPxxxx$C_3$xPPxxdfgxxd$C_4$xWxxx$C_5C_6$xx gxxx (4) [Rkeq]C1[Hkerd]x[Kreq]x[Gast][Hkerd]C2 [Flyiva][Pasgt][Kreq]xx[Ivlam]$C_3$[Livmfa] [Pasgt][Pasgt]xx[Denqa][Flyivam][Gasted]xx [Denqa]$C_4$x[Wyflvai]xxx$C_5C_6$ (5) [δ]$C_1$[δh]x[δ]x[χ][δh]$C_2$[αβ][χp][δ]xx[β]$C_3$[β] [χp][χp]xx[φqa][αβ][χed]xx[φqa]$C_4$x[αβ]xxx$C_5C_6$ In some embodiments, Myotoxin domain variants comprise sequences substantially identical to any of the above-described sequences.

To date, at least 14 naturally occurring Myotoxin domains have been identified based on cDNA sequences. Exemplary proteins containing the naturally occurring Myotoxin domains include, e.g., rattlesnake venom. Myotoxin domains are further described in, e.g., Griffin and Aird, *FEBS Lett.* 274(1-2):43-7 (1990) and Samejima et al., *Toxicon* 29(4-5): 461-8 (1991).

Delta Atracotoxin domains contain about 30-50 or 30-65 amino acids. In some embodiments, the domains comprise about 35-55 amino acids and in some cases about 40 amino acids. Within the 35-55 amino acids, there are typically about 4 to about 8 cysteine residues. Of the cysteines, disulfide bonds typically are found between the following cysteines: C1 and C4, C2 and C5, C3 and C6. Clusters of these repeats make up a ligand binding domain, and differential clustering can impart specificity with respect to the ligand binding.

Exemplary Delta Atracotoxin domain sequences and consensus sequences are as follows:

(1) $C_1xxxxxxxC_2xxxxxxxxxxxxC_3C_4C_5xxxC_6xxxxxxxxxxxC_7x$ xxxxxxxxx$C_8$ (2) $C_1xxxxxWC_2GxxxxC_3C_4C_5PxxC_6xxxWyxxxxxC_7xxxxxxxx$ xxx$C_8$ (3) $C_1xxxxxWC_2GkxedC_3C_4C_5PmkC_6ixaWyxqxgxC_7qxtixxx$ xkx$C_8$ (4) $C_1$x[krqe]xxx[wyflai]$C_2$G[Kr]x[Ed][De]$C_3C_4C_5$P [Mliva][Kr]$C_6$[Ivla]x[Astg]W[Yfl]x[Qekrd]x [Gast]x$C_7$[Qkerd]x[Tasvi][Ivla][stav][agst] [livm][fwyl][Kr]x$C_8$ (5) $C_1$x[δ]xxx[αβ]$C_2$G[Kr]x[Ed][De]$C_3C_4C_5$P[β][Kr]$C_6$ [β]x[χ]W[α]x[δ]x[χ]x$C_7$[δ]x[ϵi][β][ϵ][χ][β][α] [Kr]x$C_8$ In some embodiments, Delta Atracotoxin domain variants comprise sequences substantially identical to any of the above-described sequences.

To date, at least 6 naturally occurring Delta Atracotoxin domains have been identified based on cDNA sequences. Exemplary proteins containing the naturally occurring Delta atracotoxin domains include, e.g., sodium channel inhibitors. Delta Atracotoxin domains are further described in, e.g., Gunning et al., *FEBS Lett.* 554(1-2):211-8 (2003); Alewood et al., *Biochemistry* 42(44):12933-40 (2003); Corzo et al., *FEBS Lett.* 547(1-3):43-50 (2003); and Maggio and King, *Toxicon* 40(9):1355-61 (2002).

Toxin 1 (snake) domains contain about 30-80 or 30-75 amino acids. In some embodiments, the domains comprise about 35-55 amino acids and in some cases about 40 amino acids. Within the 35-55 amino acids, there are typically about 4 to about 8 cysteine residues. Clusters of these repeats make up a ligand binding domain, and differential clustering can impart specificity with respect to the ligand binding.

Exemplary Toxin 1 (snake) domain sequences and consensus sequences are as follows:

(1) $C_1$xxxxx(xxxx)xxxxxxxx$C_2$xxxxxx$C_3$x(x)xxxxx(xxC)x xxxxxxxxxx$C_4$xxx$C_5$xxxxx(x)xxxxxx$C_6C_7$xxxx$C_8$ (2) $C_1$xxxxx(xxxx)xxxxxxxx$C_2$xxxxxx$C_3$x(x)kxxxx(xxC)x xxxxxxxxxGC$_4$xxx$C_5$Pxxxx(x)xxxxxx$C_6C_7$xxdx$C_8$N (3) $C_1$xxxxx(xxxx)xxxxxxxx$C_2$pxgxxx$C_3$y(x)kxxxx(xxC)x xxxxxxxxxGC$_4$xxt$C_5$Pxxxx(x)xxxxxx$C_6C_7$xtdx$C_8$N (4) $C_1$[vlyfh]xxxx(xxx)xxxxx$C_2$[Pras]x[Ge]x[Ndke]x $C_3$[Yf](x)[Kres]x[wfsth]xx(xxC)xx[rpkl]xxx [ivly]x[rlk]GC$_4$[asvt][Ade][tsva]$C_5$Pxxxx(x)xxx [ivly]x$C_6C_7$x[Tsgi][Den][knrde]$C_8$N (5) $C_1$[vαh]xxxx(xxx)xxxxx$C_2$[Pras]x[Ge]x[φk]x$C_3$[α] (x)[Kres]x[wfsth]xx(xxC)xx[rpkl]xxx[vily]x -continued

[rlk]GC$_4$[ε][Ade][ε]C$_5$Pxxxx(x)xxx[vily]xC$_6$C$_7$x

[Tsgi][φ][δn]C$_8$N

In some embodiments, Toxin 1 (snake) domain variants comprise sequences substantially identical to any of the above-described sequences.

To date, at least 334 naturally occurring Toxin 1 (snake) domains have been identified based on cDNA sequences. Exemplary proteins containing the naturally occurring Toxin 1 (snake) domains include, e.g. snake toxins that bind to nicotinic acetylcholine receptors. Toxin 1 (snake) domains are further described in, e.g. Jonassen et al., *Protein Sci* 4:1587-1595 (1995) and Dufton, *J. Mol. Evol.* 20:128-134 (1984).

Toxin 5 (scorpion short) domains contain about 30-50 or 30-65 amino acids. In some embodiments, the domains comprise about 35-55 amino acids and in some cases about 35 amino acids. Within the 35-55 amino acids, there are typically about 4 to about 8 cysteine residues. Clusters of these repeats make up a ligand binding domain, and differential clustering can impart specificity with respect to the ligand binding.

Exemplary Toxin 5 (scorpion short) domain sequences and consensus sequences are as follows:

(1) C$_1$xxC$_2$xxxxxxxxxxxC$_3$xxC$_4$C$_5$xxx(x)xxxC$_6$xxxxC$_7$xC$_8$ (2) C$_1$xPC$_2$xxxxxxxxxxxC$_3$xxC$_4$C$_5$xxx(x)xGxC$_6$xxxxC$_7$xC$_8$ (3) C$_1$xPC$_2$fttxxxxxxxxC$_3$xxC$_4$C$_5$xxx(x)xGxC$_6$xxxqC$_7$xC$_8$ (4) C$_1$xPC$_2$[Flyiva][Tasv][Tasv]x[Pastv]x[mtlvia]xx xC$_3$xxC$_4$C$_5$[Gkea][Grka][rki]([Gast])x[Gast]xC$_6$x

[gsat][Pyafl][Qkerd]C$_7$[livmfa]C$_8$ (5) C$_1$xPC$_2$[αβ][ε][ε]x[εp]x[βt]xxxC$_3$xxC$_4$C$_5$[Gkea]

[Grka][rki]([χ])x[χ]xC$_6$x[χ][Pyafl][δ]C$_7$[β]C$_8$

In some embodiments, Toxin 5 (scorpion short) domain variants comprise sequences substantially identical to any of the above-described sequences.

To date, at least 15 naturally occurring Toxin 5 (scorpion short) domains have been identified based on cDNA sequences. Exemplary proteins containing the naturally occurring Toxin 5 (scorpion short) domains include, e.g., secreted scorpion short toxins.

Toxin 6 (scorpion) domains contain about 15-50 or 20-65 amino acids. In some embodiments, the domains comprise about 15-35 amino acids and in some cases about 25 amino acids. Within the 35-55 amino acids, there are typically about 4 to about 6 cysteine residues. Clusters of these repeats make up a ligand binding domain, and differential clustering can impart specificity with respect to the ligand binding.

Exemplary Toxin 6 (scorpion) domain sequences and consensus sequences are as follows:

(1) C$_1$xxC$_2$xxxC$_3$xxxxxxxxxC$_4$xxxxC$_5$xC$_6$ (2) C$_1$xxC$_2$PxhC$_3$xGxxxxPxC$_4$xxGxC$_5$xC$_6$ (3) C$_1$eeC$_2$PxhC$_3$xGxxxxPxC$_4$ddGxC$_5$xC$_6$ (4) C$_1$[Edknsa][Edknsa]C$_2$[Pasgte][Mlivaf]

[Hkerasdyflqnt]C$_3$[Kreq][Gasted][Kreq][Neda]

[Astvgx][knerd][Pasgtekd][Tasvgl]C$_4$[Densak]

[Densak][Gasted][Vilaa]C$_5$[Neda]C$_6$ (5) C$_1$[φksa][φksa]C$_2$[χep][β][Hkerasdyflqnt]C$_3$[δ]

[χed][δ][φa][εgx][knerd][χedkp][εgl]C$_4$[φsak]

[φsak][χed][β]C$_5$[φa]C$_6$

In some embodiments, Toxin 6 (scorpion) domain variants comprise sequences substantially identical to any of the above-described sequences.

To date, at least 7 naturally occurring Toxin 6 (scorpion) domains have been identified based on cDNA sequences. Exemplary proteins containing the naturally occurring Toxin 6 (scorpion) domains include, e.g., scorpion toxins and proteins that block calcium-activated potassium channels. Toxin 6 (scorpion) domains are further described in, e.g., Zhu et al., *FEBS Lett* 457:509-514 (1999) and Xu et al., *Biochemistry* 39:13669-13675 (2000).

Toxin 7 (spider) domains contain about 30-50 or 30-65 amino acids. In some embodiments, the domains comprise about 35-55 amino acids and in some cases about 40 amino acids. Within the 35-55 amino acids, there are typically about 4 to about 8 cysteine residues. Clusters of these repeats make up a ligand binding domain, and differential clustering can impart specificity with respect to the ligand binding.

Exemplary Toxin 7 (spider) domain sequences and consensus sequences are as follows:

(1) C$_1$[vlai]x[edkn]xxxC$_2$xxxxxxxxC$_3$C$_4$xxxxC$_5$xC$_6$xxxxx

C$_7$xC$_8$ (2) C$_1$xxxxxxxC$_2$xxWxxxxC$_3$C$_4$xxxYC$_5$xC$_6$xxxPxC$_7$xC$_8$ (3) C$_1$xxxxxxxC$_2$xdWxgxxC$_3$C$_4$xgxyC$_5$xC$_6$xxxPxC$_7$xC$_8$ (4) C$_1$[vlai]x[denk]xxxC$_2$x[Dens][Wyfli]xxxxC$_3$C$_4$

[deg][ged][yfmliv][Ywflh]C$_5$[stna]C$_6$xxx[Pgast]

xC$_7$xC$_8$[rk]

(5) C$_1$[β]x[δk]xxxC$_2$x[βs][αi]xxxxC$_3$C$_4$[deg][ged]

[αβ][αh]C$_5$[astn]C$_6$xxx[χp]xC$_7$xC$_8$[rk]

In some embodiments, Toxin 7 (spider) domain variants comprise sequences substantially identical to any of the above-described sequences.

To date, at least 14 naturally occurring Toxin 7 (spider) domains have identified based on cDNA sequences. Exemplary proteins containing the naturally occurring Toxin 7 (spider) domains include, e.g., short spider neurotoxins. Toxin 7 (spider) domains are further described in, e.g., Skinner et al., *J. Biol. Chem.* (1989) 264:2150-2155 (1989).

Toxin 9 (spider) domains contain about 30-50 or 30-65 amino acids. In some embodiments, the domains comprise about 35-55 amino acids and in some cases about 40 amino acids. Within the 35-55 amino acids, there are typically about 4 to about 8 cysteine residues. Clusters of these repeats make up a ligand binding domain, and differential clustering can impart specificity with respect to the ligand binding.

Exemplary Toxin 9 (spider) domain sequences and consensus sequences are as follows:

(1) $C_1xx(x)xxxxxC_2xxxxxxxC_3C_4xxx(x)xC_5xC_6xxxxxxC_7xC_8$ (2) $C_1xx(x)xYxxC_2xxGxxxC_3C_4xxR(x)xC_5xC_6xxxxxNC_7xC_8$ (3) $C_1[vila][agd](x)x[Yqfl][kegd][kret]C_2x[kwy][Gp]xx[prk]C_3C_4x[gde][Rck](x)[pamg]C_5xC_6x[ilmv][mg]xx[Nde]C_7xC_8$ (4) $C_1[\beta][agd](x)x[Yqfl][kegd][kret]C_2x[kwy][Gp]xx[prk]C_3C_4x[gde][Rck](x)[pamg]C_5xC_6x[\beta][mg]xx[\phi]C7xC_8$ In some embodiments, Toxin 9 (spider) domain variants comprise sequences substantially identical to any of the above-described sequences.

To date, at least 13 naturally occurring Toxin 9 (spider) domains have identified based on cDNA sequences. Exemplary proteins containing the naturally occurring Toxin 9 (spider) domains include, e.g., spider neurotoxins and calcium ion channel blockers.

CART Domains

CART domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Of the six cysteines, disulfide bonds typically are found between the following cysteines: C1 and C3, C2 and C5, C4 and C6. Clusters of these repeats make up a ligand binding domain, and differential clustering can impart specificity with respect to the ligand binding.

Exemplary CART domain sequences and consensus sequences are as follows:

(1) $C_1xxxxxC_2xxxxxxxxxxxC_3xC_4xxxxxC_5xxxxxxC_6$ (2) $C_1xxGxxC_2xxxxGxxxxxxC_3xC_4PxGxxC_5xxxxxxC_6$ (3) $C_1dxGeqC_2axrkGxrxgkxC_3dC_4PrGxxC_5nxfllkC_6$ (4) $C_1[Denq]x[Gast][Ednq][Qkerd]C_2[Astg][Ivlam][Rkqe][Krqe][Gast]x[Rkqea]x[Ivla][Gast][Krqe][lmivfa]xC_3[Denq]C_4P[Rkqae][Gast]xxC_5[Ned]x[Fyliva][Livmfa][Livmfa][Krqe]C_6[Livmfa]$ (5) $C_1[\phi q]x[\chi][\phi q][\delta]C_2[\chi][\beta][\delta][\delta][\chi]x[\delta a]x[\beta][\chi][\delta e][\beta]xC_3[\phi q]C_4P[\delta a][\chi]xxC_5[\phi]x[\alpha\beta][\beta][\beta][\delta]C_6[\beta]$ In some embodiments, CART domain variants comprise sequences substantially identical to any of the above-described sequences.

To date, at least 9 naturally occurring CART domains have identified based on cDNA sequences. Exemplary proteins containing the naturally occurring CART domains include, e.g., cocaine and amphetamine regulated transcript type I protein (CART) sequences. CART domains are further described in, e.g., Kristensen et al., *Nature* 393(6680):72-6 (1998).

Fn Domains

Fn1 domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Fn1 domain sequences and consensus sequences are as follows:

(1) $C_1xx(x)xxxxxxxxxxxxxxxxx(x)xxxxx(x)C_2xC_3xxxxxxxxxC_4$ (2) $C_1xx(x)xxxxxYxxxxxWxxxxx(x)xxxxx(x)C_2xC_3xGxxxxxxxC_4$ (3) $C_1xd(x)xxxxxYxxgxxWxxxxx(x)gxxxx(x)C_2xC_3xGxxxgxxxC_4$ (4) $C_1x[Detv](x)xx[grqlv]xx[Yf]xx[Gnhq][deqmx][wyfl]x[rk]xxx(x)[gsan]xxxx(x)C_2xC_3[lfyiv]Gxxx[Gpsw]x[wafivl]xC_4$ (5) $C_1x[Detv](x)xx[grqlv]xx[\alpha]xx[Gnhq][deqmx[\alpha]x[rk]xxx(x)[gsan]xxxx(x)C_2xC_3[\alpha\beta]Gxxx[Gpsw]x[\alpha\beta]xC_4$ In some embodiments, Fn1 domain variants comprise sequences substantially identical to any of the above-described sequences.

To date, at least 243 naturally occurring Fn1 domains have identified based on cDNA sequences. Exemplary proteins containing the naturally occurring Fn1 domains include, e.g., human tissue plasminogen activator. Fn1 domains are further described in, e.g., Bennett et al., *J Biol. Chem.* 266(8):5191-201 (1991); Baron et al., *Nature*. 345(6276):642-6 (1990); and Smith et al., *Structure* 3(8):823-33 (1995).

Fn2 domains contain about 30-50 or 30-65 amino acids. In some embodiments, the domains comprise about 35-55 amino acids and in some cases about 40 amino acids. Within the 35-55 amino acids, there are typically about 4 to about 6 cysteine residues. Clusters of these repeats make up a ligand binding domain, and differential clustering can impart specificity with respect to the ligand binding.

Exemplary Fn2 domain sequences and consensus sequences are as follows:

(1) $C_1xxxxxxxxxxxxxxC_2xxxxx(x)xxxxxC_3xxxxxxxxxxxxxxxC_4$ (2) $C_1xxPFxxxxxxxxxxC_2xxxxx(x)xxxxWC_3xxxxxxxxxDxxxxxC_4$ (3) $C_1xfPFxxxxxxyxxC_2xxxgx(x)xxxxWC_3xttxnyxxDxxxxxC_4$ (4) $C_1x[Flyi]P[Fy]x[yf]xxxx[Yflh]xxC_2[Tivl]xx[Gas][Rsk](x)xxxxWC_3[sag][Tli][Tsda]x[Nde][Yfl][detv]xDxx[wfyl][gks][fy]C_4$ -continued (5) $C_1x[\alpha i]P[\alpha]x[\alpha]xxxx[\alpha h]xxC_2[Tivl]xx[Gas][Rsk]$ (x) $xxxxWC_3[gas][Tli][Tsda]x[den][\alpha][detv]xDxx$
$[\alpha][gks][\alpha]C_4$ In some embodiments, Fn2 domain variants comprise sequences substantially identical to any of the above-described sequences.

To date, at least 248 naturally occurring Fn2 domains have identified based on cDNA sequences. Exemplary proteins containing the naturally occurring Fn2 domains include, e.g., blood coagulation factor XII, bovine seminal plasma proteins PDC-109 (BSP-A1/A2) and BSP-A3; cation-independent mannose-6-phosphate receptor; mannose receptor of macrophages; 180 Kd secretory phospholipase A2 receptor; DEC-205 receptor; 72 Kd and 92 Kd type IV collagenase (EC:3.4.24.24); and hepatocyte growth factor activator. Fn2 domains are further described in, e.g., Dean et al., *PNAS USA* 84(7):1876-80 (1987).

Gamma Thionin Domains

Gamma thionin domains contain about 30-50 or 30-65 amino acids. In some embodiments, the domains comprise about 35-55 amino acids and in some cases about 50 amino acids. Within the 35-55 amino acids, there are typically about 4 to about 8 cysteine residues. Clusters of these repeats make up a ligand binding domain, and differential clustering can impart specificity with respect to the ligand binding.

Exemplary Gamma thionin domain sequences and consensus sequences are as follows:

(1) $C_1xxxxxxxxxxxC_2xxxxxC_3xxxC_4xxxxxx (xxxx) xxxC_5xx$
    $(xxxx) xxxxC_6xC_7xxxC_8$ (2) $C_1xxxSxxxxGxC_2xxxxxC_3xxxC_4xxxxxx (xxxx) xGxC_5xx$
    $(xxxx) xxxxC_6xC_7xxxC_8$ (3) $C_1xxxSxxfxGxC_2xxxxxC_3xxxC_4xxexxx (xxxx) xGxC_5xx$
    $(xxxx) xxxrC_6xC_7xxxC_8$ (4) $C_1xxxSxx[Fwyh]x[Gfy]xC_2xxxxxC_3xxxC_4xx[Ekwn]xxx$
    $(xxxx) xGxC_5xx (xxxx) xxx[rkya]C_6xC_7xxxC_8$ (5) $C_1xxxSxx[\alpha h]x[Gfy]xC_2xxxxxC_3xxxC_4xx[Ekwn]xxx$
    $(xxxx) xGxC_5xx (xxxx) xxx[rkya]C_6xC_7xxxC_8$ In some embodiments, Gamma thionin domain variants comprise sequences substantially identical to any of the above-described sequences.

To date, at least 133 naturally occurring Gamma thionin domains have identified based on cDNA sequences. Exemplary proteins containing the naturally occurring Gamma thionin domains include, e.g., animal, bacterial, fungal toxins from a broad variety of crop plants. Gamma thionin domains are further described in, e.g., Bloch et al., *Proteins* 32(3):334-49 (1998).

b. Production of Synthetic Cysteine Loop Domain Multimers

Synthetic monomers or multimers can be produced by any method that produces protein sequence variants. Examples of variant generation can be found, for example, in U.S. Patent Application Nos. 2003/0082630; 2003/0157561; 2005/0048512; 2005/0053973; 2005/0089932; 2005/0164301; 2006/0008844 the disclosures of each of which are hereby incorporated herein by reference in their entirety for all purposes.

Methods for generating multimers from monomer domains can include joining the selected domains with at least one linker to generate at least one multimer, e.g., the multimer can comprise at least two of the monomer domains and the linker. The multimer(s) can then be screened for an improved avidity or affinity or altered specificity for the desired ligand or mixture of ligands as compared to the selected monomer domains.

Methods for producing monomer or multimer variants can comprise, e.g., any or all of the following steps: providing a plurality of different nucleic acids, where each nucleic acid encoding a monomer domain; translating the plurality of different nucleic acids, which provides a plurality of different monomer domains; screening the plurality of different monomer domains for binding of the desired ligand or mixture of ligands; identifying members of the plurality of different monomer domains that bind the desired ligand or mixture of ligands, which provides selected monomer domains; joining the selected monomer domains with at least one linker to generate at least one multimer, wherein the at least one multimer comprises at least two of the selected monomer domains and the at least one linker; and, screening the at least one multimer for an improved affinity or avidity or altered specificity for the desired ligand or mixture of ligands as compared to the selected monomer domains.

Variation can be introduced into either monomers or multimers. An example of improving monomers includes intra-domain recombination in which two or more (e.g., three, four, five, or more) portions of the monomer are amplified separately under conditions to introduce variation (for example by shuffling or other recombination method) in the resulting amplification products, thereby synthesizing a library of variants for different portions of the monomer. By locating the 5' ends of the middle primers in a "middle" or "overlap" sequence that both of the PCR fragments have in common, the resulting "left" side and "right" side libraries may be combined by overlap PCR to generate novel variants of the original pool of monomers. These new variants can then be screened for desired properties, e.g., panned against a target or screened for a functional effect. The "middle" primer(s) may be selected to correspond to any segment of the monomer, and will typically be based on the scaffold or one or more consensus amino acids within the monomer (e.g., cysteines such as those found in A domains).

Similarly, multimers can be created by introducing variation at the monomer level and then recombining monomer variant libraries. On a larger scale, multimers (single or pools) with desired properties may be recombined to form longer multimers. In some cases variation is introduced (typically synthetically) into the monomers or into the linkers to form libraries. This can be achieved, e.g., with two different multimers that bind to two different targets, thereby eventually selecting a multimer with a portion that binds to one target and a portion that binds a second target.

Multimer libraries can be generated, in some embodiments, by combining two or more libraries or monomers or multimers in a recombinase-based approach, where each library member comprises as recombination site (e.g., a lox site). A larger pool of molecularly diverse library members in principle harbor more variants with desired properties, such as higher target-binding affinities and functional activities. When libraries are constructed in phage vectors, which may be transformed into *E. coli*, library size ($10^9$-$10^{10}$) is limited by the transformation efficiency of *E. coli*. A recombinase/recombination site system (e.g., the Cre-loxP system) and in vivo recombination can be exploited to generate libraries that are not limited in size by the transformation efficiency of *E. coli*.

For example, the Cre-loxP system may be used to generate dimer libraries with $10^{10}$, $10^{11}$, $10^{12}$, $10^{13}$, or greater diversity. In some embodiments, *E. coli* as a host for one naïve monomer library and a filamentous phage that carries a second naïve monomer library are used. The library size in this case is limited only by the number of infective phage (carrying one library) and the number of infectible *E. coli* cells (carrying the other library). For example, infecting $10^{12}$ *E. coli* cells (1 L at OD600=1) with >$10^{12}$ phage could produce as many as $10^{12}$ dimer combinations.

Methods for generating multimers from monomer domains can include joining the selected domains with at least one linker to generate at least one multimer, e.g., the multimer can comprise at least two of the monomer domains and the linker. The multimer(s) can then be screened for an improved avidity or affinity or altered specificity for the desired ligand or mixture of ligands as compared to the selected monomer domains. A composition of the multimer produced by the method is included in the present invention.

Selection of multimers can be accomplished using a variety of techniques including those mentioned above for identifying monomer domains. Other selection methods include, e.g., a selection based on an improved affinity or avidity or altered specificity for the ligand compared to selected monomer domains. For example, a selection can be based on selective binding to specific cell types, or to a set of related cells or protein types (e.g., different virus serotypes). Optimization of the property selected for, e.g., avidity of a ligand, can then be achieved by recombining the domains, as well as manipulating amino acid sequence of the individual monomer domains or the linker domain or the nucleotide sequence encoding such domains, as mentioned in the present invention.

One method for identifying multimers can be accomplished by displaying the multimers. As with the monomer domains, the multimers are optionally expressed or displayed on a variety of display systems, e.g., phage display, ribosome display, polysome display, nucleotide-linked display (see, e.g., U.S. Pat. Nos. 6,281,344; 6,194,550; 6,207,446; 6,214,553, and 6,258,558) and/or cell surface display, as described above. Cell surface displays can include but are not limited to *E. coli*, yeast or mammalian cells. In addition, display libraries of multimers with multiple binding sites can be panned for avidity or affinity or altered specificity for a ligand or for multiple ligands.

Monomers or multimers can be screened for target binding activity in yeast cells using a two-hybrid screening assay. In this type of screen the monomer or multimer library to be screened is cloned into a vector that directs the formation of a fusion protein between each monomer or multimer of the library and a yeast transcriptional activator fragment (i.e., Gal4). Sequences encoding the "target" protein are cloned into a vector that results in the production of a fusion protein between the target and the remainder of the Gal4 protein (the DNA binding domain). A third plasmid contains a reporter gene downstream of the DNA sequence of the Gal4 binding site. A monomer that can bind to the target protein brings with it the Gal4 activation domain, thus reconstituting a functional Gal4 protein. This functional Gal4 protein bound to the binding site upstream of the reporter gene results in the expression of the reporter gene and selection of the monomer or multimer as a target binding protein. (see Chien et.al. (1991) Proc. Natl. Acad. Sci. (USA) 88:9578; Fields S, and Song O. (1989) Nature 340: 245) Using a two-hybrid system for library screening is further described in U.S. Pat. No. 5,811,238 (see also Silver S. C. and Hunt S. W. (1993) Mol. Biol. Rep. 17:155; Durfee et al. (1993) Genes Devel. 7:555; Yang et al. (1992) Science 257:680; Luban et al. (1993) Cell 73:1067; Hardy et al. (1992) Genes Devel. 6:801; Bartel et al. (1993) Biotechniques 14:920; and Vojtek et al. (1993) Cell 74:205).

Another useful screening system for carrying out the present invention is the *E. coli*/BCCP interactive screening system (Germino et al. (1993) Proc. Nat. Acad. Sci. (U.S.A.) 90:993; Guarente L. (1993) Proc. Nat. Acad. Sci. (U.S.A.) 90:1639).

Libraries comprising multimers, e.g, a library comprising about 100, 250, 500 or more members produced by the methods of the present invention or selected by the methods of the present invention are provided. In some embodiments, one or more cell comprising members of the libraries, are also included. Libraries of the recombinant polypeptides are also a feature of the present invention, e.g., a library comprising about 100, 250, 500 or more different recombinant polypeptides.

c. Expression of Polypeptides in Prokaryotic Host Cells

The polypeptides used in the present methods can be expressed in prokaryotic host cells according to methods well known in the art. See, for example, Sambrook and Russell, *Molecular Cloning: A Laboratory Manual*, 2000, Cold Spring Harbor Laboratory Press; Ausubel, et al., *Current Protocols in Molecular Cloning*, 1987-2006, John Wiley & Sons; *Protein Expression: A Practical Approach*, Higgins and Hames, Eds., 1999, Oxford University Press; *Production of Recombinant Proteins: Novel Microbial and Eukaryotic Expression Systems*, Gellissen, ed., 2005, John Wiley & Sons.

The polypeptides can be expressed in any appropriate prokaryotic host cell, including gram-negative and gram-positive host cells. Appropriate host cells include without limitation, for example, *E. coli, Bacillus, Campylobacter, Pseudomonas fluorescens* and the like. Though substrains are not necessary, bacterial strains specially designed for the expression of polypeptides with disulfide bonds also find use, for example, Origami™ and Rosetta-gami™ *E. coli* host strains commercially available from Novagen (EMDBiosciences), San Diego, Calif.

The polypeptides can be cloned into any appropriate prokaryotic expression vector. Numerous vectors for expression of proteins in prokaryotic host cells are known in the art and commercially available. For example, numerous variations of T7 and pET vectors are available for purchase from Invitrogen, Carlsbad, Calif. and Novagen (EMDBiosciences), San Diego, Calif.

The polypeptides can be expressed in the cytoplasm or trafficked to the periplasmic space. When expressing in the cytoplasm, the polypeptides do not have a signal peptide or secretory signal sequence. When expressing a polypeptide to be trafficked to the periplasmic space, the polypeptide will be operably linked to a secretory signal sequence at its N-terminus, including but not limited to, a pelB, OmpA, or β-lactamase leader sequence. See, Georgiou and Segatori, *Curr Opin Biotechnol.* (2005) 16(5):538-45; Choi and Lee, *Appl Microbiol Biotechnol.* (2004) 64(5):625-35; and Mergulhao, et al., *Biotechnol Adv.* (2005) 23(3): 177-202. Expression vectors for directing recombinantly expressed polypeptides to the periplasmic space are commercially available from, for example, Novagen (EMDBiosciences), San Diego, Calif. and Genlantis, San Diego, Calif.

Expression of the polypeptides of interest in a prokaryotic host can be inducible, for example, upon exposure to isopropyl thiogalactoside (IPTG). After exposure to an expression induction moiety for an appropriate amount of time, for example, 2, 4, 6, 8, 10, 12, 24 hours, the prokaryotic host cells are subject to heat lysis.

d. Heat Lysis

After expressing the recombinant multimeric polypeptides for an appropriate amount of time, the prokaryotic host cells are subject to a sufficient amount of heat for a sufficient amount of time to effect lysis of at least about 50% of the host cells. Due to the heat stability of the proteins of the invention, the desired proteins will not be substantially denatured by the heat and therefore will allow for a purification step resulting in high purity (e.g., at least 50% or more, for example, 60%, 70%, 80% or 90%, of protein in cytoplasm of prokaryotic cell is recovered in the separation step and available for subsequent purification steps). The heat lysis step can be followed by a fast cooling step to prevent most other proteins from renaturing.

The level of heat and the amount of time necessary to induce cell lysis are inversely related. For example, higher temperatures require shorter time durations to achieve the same percentage of cell lysis. Conversely, longer time durations do not require as high of temperature exposures.

The prokaryotic host cells are generally exposed to temperatures of at least about 50° C. and as high as about 105° C., for example, in the range of about 50-100° C., 65-99° C., 65-85° C., 75-85° C. or 75-95° C., for example, about 50° C., 55° C., 65° C., 70° C., 75° C., 80° C., 85° C., 90° C., 95° C., 96° C., 97° C., 98° C., 99° C., 100° C., or 105° C.

The prokaryotic host cells are generally exposed to heat temperatures for at least about 1 minute to about 50 minutes, for example, about 1-40, 1-10, 2-20, 5-10, 5-15 or 10-15 minutes, for example, about 1, 2, 3, 4, 5, 8, 10, 12, 15, 18, 20, 22, 25, 28, 30, 32, 35, 38 or 40 minutes. In some embodiments, the prokaryotic host cells are subjected to "flash" heat lysis. For example, the host cells are exposed to sufficiently heated temperatures for at least one second to about 1 min, or 1-60 seconds, for example, about 1, 2, 3, 4, 5, 8, 10, 12, 15, 18, 20, 22, 25, 28, 30, 32, 35, 38, 39, 40, 41, 42, 43, 44, 45, 46, 47, 48, 49, 50, 51, 52, 53, 54, 55, 56, 57, 58, 59 or 60 seconds or any fractions thereof.

In some embodiments, the prokaryotic cells are exposed to 95° C. for 10 minutes to effect lysis of at least about 50% of the host cells.

In some embodiments, the prokaryotic host cells (lysed and unlysed) are subjected to cooling immediately following exposure to heat. For cooling, the cells are exposed to decreasing temperatures or a decreased temperature at a rate sufficient to promote precipitation of the host cell components other than the multimeric polypeptides while retaining maximal solubility of the multimeric polypeptides. For example, in some embodiments, the cooling step comprises subjecting the prokaryotic host cells to a temperature of less than about 65° C., for example, about 60° C., 55° C., 50° C., 45° C., 40° C., 35° C., 30° C., 25° C., 20° C., 15° C., 10° C., 5° C., or 0° C. for at least about 1 minute. In some embodiments, the cooling step comprises subjecting the prokaryotic host cells to a decreasing temperature gradient, wherein the temperature is decreased by at least about 1 degree (Celsius) per minute, for at least about 5 minutes. The decreasing temperature gradient, can be, but need not be linear. In some embodiments, the cooling step comprises subjecting the prokaryotic host cells to an incubation at a temperature of from about −10° C. to about 10° C., for example, by placing the host cells in an ice bath.

In some embodiments, a continuous flow heating process to purify the polypeptides from bacterial cell cultures is used. For example, a cell suspension can passed through a stainless steel coil submerged in a water bath set to a temperature resulting in lysis of the bacteria (e.g., about 65-100° C.). The lysed effluent can then be routed to a cooling bath to obtain rapid cooling and prevent renaturation of denatured E. coli proteins. Native E. coli proteins denature and are prevented from renaturing, but the recombinant polypeptides used in the present methods do not denature under these conditions due to the exceptional stability of their scaffold. The heating time is controlled by adjusting the flow rate and length of the coil. This approach yields active proteins with high yield and exceptionally high purity (e.g., >80%) compared to alternative approaches and is amenable to large scale production of clinical material.

The extent of cell lysis can be determined by plating host cells from the cultures, with equal volume aliquots taken before and after exposure to a heat lysis treatment. Serial dilutions of cell cultures can be plated on appropriate agar plates (e.g., LB plates with an appropriate antibiotic). The number of colonies that grow from an equivalent dilution after about 16-24 hours from the control unexposed cultures are compared to the heat lysis exposed cultures. The percent cell lysis is calculated as follows from cultures of an equivalent dilution:

$$\frac{\text{(the number of colonies that grow from a heat lysis exposed culture)}}{\text{(the number of colonies that grow from a control unexposed culture)}} \times 100$$

e. Separation

The recombinantly expressed polypeptides are then separated from the other host cell components. This can be accomplished in any manner known in the art. For example, the soluble and insoluble fractions can be separated by centrifugation. Precipitated denatured proteins and cell membrane components will pellet with centrifugation and the expressed polypeptides will remain in the supernatant. In another embodiment, the soluble and insoluble fractions can be separated using a filter that only allows the soluble fraction to pass through.

In another embodiment, the expressed polypeptides are removed by exposure to a substrate (e.g., beads) having an attached purification binding moiety. For example, the recombinant peptides can be expressed as fusion proteins with an affinity purification tag (e.g., 6×HisTag, FLAG tag, myc, glutathione S-transferase, etc.), and then selectively separated from other host cell components by exposure to a substrate covalently linked to a purification binding moiety (e.g., Ni, an antibody against FLAG or myc or glutathione, etc.). Affinity purification techniques are well known in the art. Additional purification steps following initial separation can also be performed.

3. Screening Methods a. Plurality of Cultures

The present methods are well suited to be carried out in a high-throughput capacity, for example, for screening purposes. A plurality of cultures of prokaryotic host cells, each culture recombinantly expressing a different multimeric polypeptide, can be concurrently grown in multiwell plates or a plurality of culture tubes. For example cultures can be simultaneously grown in 6-well, 12-well, 24-well, 48-well, 96-well, 192-well, 384-well, 768-well or 1536-well multiwell plates. Heat lysis treatment of the multiple cultures can be carried out by subjecting the multiwell plates or plurality of culture tubes to elevated temperatures for an appropriate period of time. Alternatively, automated systems for liquid handling can route the individual cultures through heat conditions and cooling conditions, as appropriate. The polypeptides isolated by the present methods can be separated using any techniques known in the art, including centrifugation, filtering, or affinity purification, as described above. Automated systems for carrying out the present methods in a high-throughput capacity are commercially available, for example, from Caliper Life Sciences, Hopkinton, Mass.

b. Screening for a Desired Function

The separated polypeptides can be screened in a parallel manner for a desired function, for example the ability to specifically bind to a target molecule. Using the multimeric proteins of the present invention, diversity can be generated from the domain scaffolds (e.g., permutations of A domains) and screened for desired binding to non-natural ligand of the domains. See, for example, U.S. Patent Publication Nos.: 2003/0082630; 2003/0157561; 2005/0048512; 2005/0053973; 2005/0089932; 2005/0164301; 2006/0008844 the disclosures of each of which are hereby incorporated herein by reference in their entirety for all purposes.

Target molecules can be proteins, nucleic acids, lipids, carbohydrates, small organic molecules, or any other molecule capable of recognition by a polypeptide domain. For example, a target molecule can include a chemical compound (i.e., non-biological compound such as, e.g., an organic molecule, an inorganic molecule, or a molecule having both organic and inorganic atoms, but excluding polynucleotides and proteins), a mixture of chemical compounds, an array of spatially localized compounds, a biological macromolecule, a bacteriophage peptide display library, a polysome peptide display library, an extract made from a biological materials such as bacteria, plants, fungi, or animal (e.g., mammalian) cells or tissue, a protein, an enzyme, a receptor, a toxin, a peptide hormone, a cell, a virus, or the like. Other target molecules include, e.g., a whole cell, a whole tissue, a mixture of related or unrelated proteins, a mixture of viruses or bacterial strains or the like. Target molecules can also be defined by inclusion in screening assays described herein or by enhancing or inhibiting a specific protein interaction (i.e., an agent that selectively inhibits a binding interaction between two predetermined polypeptides).

Specifically binding multimeric polypeptides can bind a target molecule with an equilibrium dissociation constant (Kd) of less than (i.e., stronger binding than) about $10^{-5}$ M, $10^{-6}$ M, $10^{-7}$ M, $10^{-8}$ M, $10^{-9}$ M, $10^{-10}$ M, $10^{-11}$ M or $10^{-12}$ M. The ability of a plurality of multimeric polypeptides to bind a target molecule can be simultaneously measured using multiwell plates and automated high-throughput methods.

In some embodiments, the multimeric polypeptides are screened for their ability to directly bind to a target molecule. This can be carried out using assays that directly detect or indirectly detect the binding of the polypeptide to the target molecule. In a direct detection assay, multimeric polypeptides can themselves be labeled (e.g., with a fluorophore, a chromophore, an enzyme, a radioisotope), and their binding to the target molecule directly detected. Alternatively, in an indirect detection assay, binding of the multimeric polypeptides is detected by the binding of a labeled secondary moiety, for example, a labeled antibody that specifically binds an epitope on the multimeric polypeptide (e.g., a labeled anti-FLAG tag, anti-HA or anti-myc antibody). The binding assays can be carried out using techniques similar to those established for ELISA. See, for example, Harlow and Lane, *Using Antibodies: A Laboratory Manual,* 1998, Cold Spring Harbor Laboratory; and Crowther, *The ELISA Guidebook,* 2000, Humana Press.

In some embodiments, the multimeric polypeptides are screened for their ability to compete with another cognate binding moiety (e.g., a ligand) in binding to a target molecule. In such competition assays either the multimeric polypeptide or the cognate binding moiety can be labeled. If the multimeric polypeptide is labeled, then increased detection of signal correlates with the increased ability of the polypeptide to bind to the target molecule in the presence of the cognate binding moiety. If the cognate binding moiety is labeled, then decreased detection of signal correlates with the increased ability of the polypeptide to bind to the target molecule in the presence of the cognate binding moiety. Competition assays are well known in the art.

If the heat stable polypeptides have enzymatic activity, then this activity can be detected, for example, by monitoring the conversion of an appropriate substrate. If the heat stable polypeptides can induce intracellular signaling, this activity can also be detected, for example, by monitoring downstream intracellular mediators, ion influx, and/or gene expression in a cell.

EXAMPLES

The following examples are offered to illustrate, but not to limit the claimed invention.

Example 1

This example demonstrates that conditions for heat treatment do not influence binding functionality of multimeric polypeptides used in the present methods.

A trimeric multimer polypeptide (comprising three non-naturally occurring A domain sequences) that specifically binds CD40 was substantially purified by exposure of the expressing *E. coli* host cells to varying elevated temperatures (65° C., 75° C., 85° C. or 95° C.) for varying time periods (5 min, 10 min, 20 min or 40 minutes). *E. coli* BL21(DE3) Gold cells containing a modified pET24b plasmid carrying the multimer gene of interest (tagged with N-terminal HA and 6×His tags) under control of an inducible T7 promoter sequence were grown to an OD of ~2. Protein expression was induced by addition of IPTG to 1 mM and cells were grown at 37° C. for 3 hours. Cells were harvested by centrifugation, resuspended in 120 mM NaCl, 20 mM Tris pH 7.5, 1 mM CaCl$_2$, and split into equal portions for high temperature lysis at the conditions listed above. Lysed cells were incubated on ice for 10 minutes, and insoluble protein was then removed by centrifugation. To determine the retention of the ability of the trimeric polypeptide to bind to CD40, a direct binding assay was carried out on the lysis supernatant. Binding was detected indirectly, using a secondary antibody against HA Tag labeled with horseradish peroxidase. Enzymatic conversion of substrate was measured in a chromogenic reaction. In a similar manner, binding of a monomer clone designed to bind to IgG was also tested.

The results are depicted in FIG. 1 and are tabulated in FIG. 2. Binding of the trimeric multimer polypeptide could be detected at all of the time and temperature combinations tested. Comparable recovery was achieved between the monomer domain polypeptide and the multimer domain polypeptide.

Example 2

Figure 3:
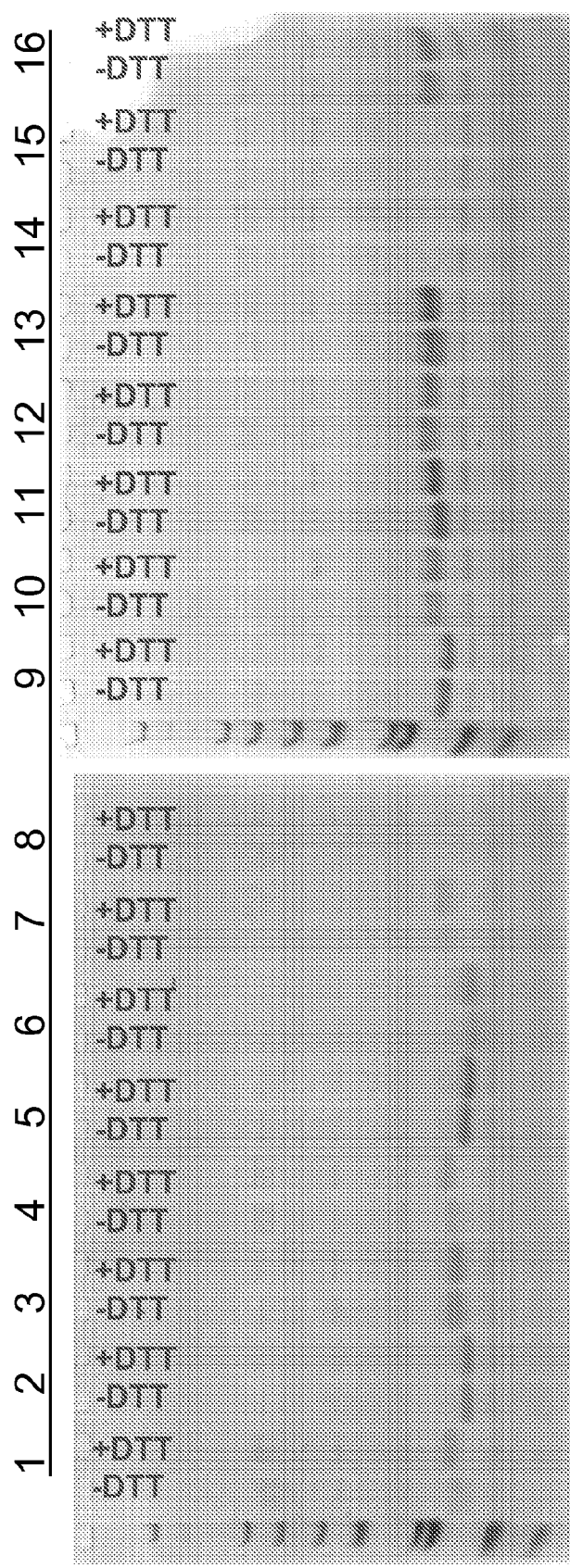
FIG. 3 illustrates a sodium dodecyl sulfate polyacrylamide gel electrophoresis (SDS-PAGE) of polypeptides expressed from a Trefoil/PD domain scaffold library and isolated using heat lysis.
Figure 4:
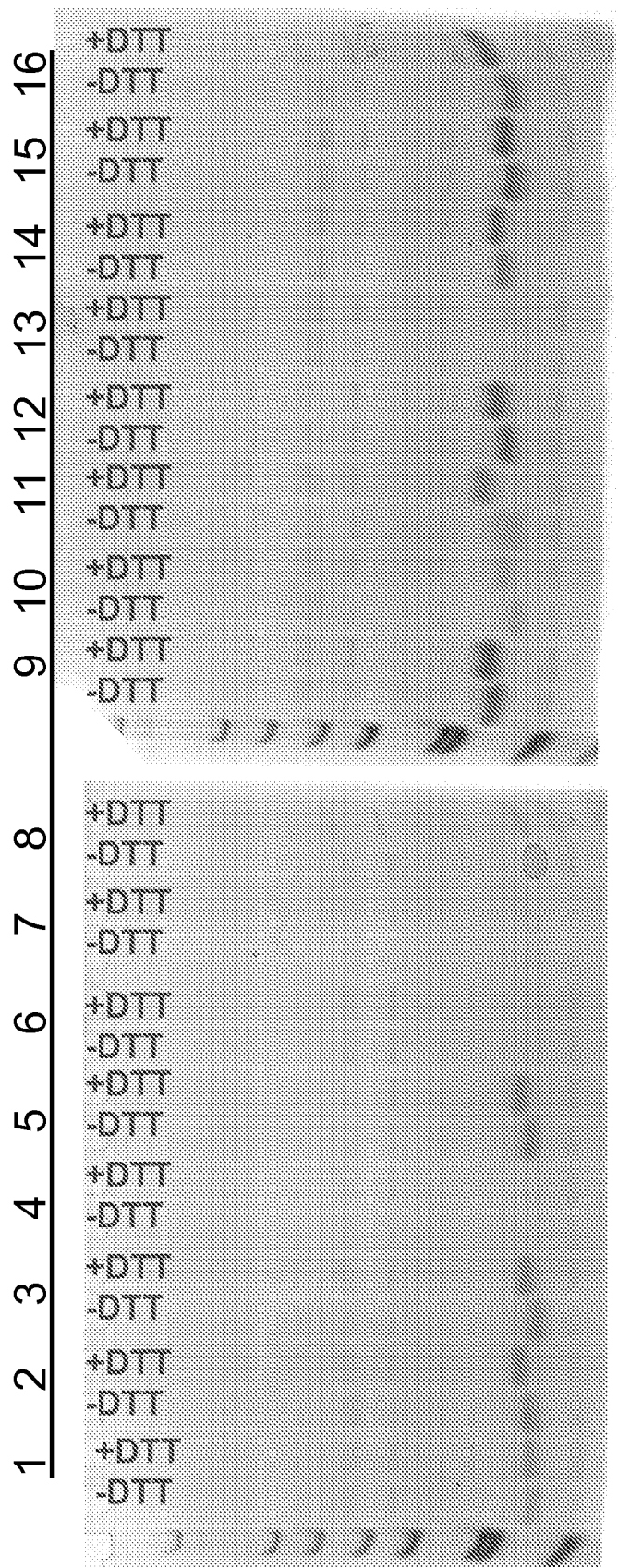
FIG. 4 illustrates an SDS-PAGE of polypeptides expressed from an integrin-beta domain scaffold library and isolated using heat lysis.
Figure 5:
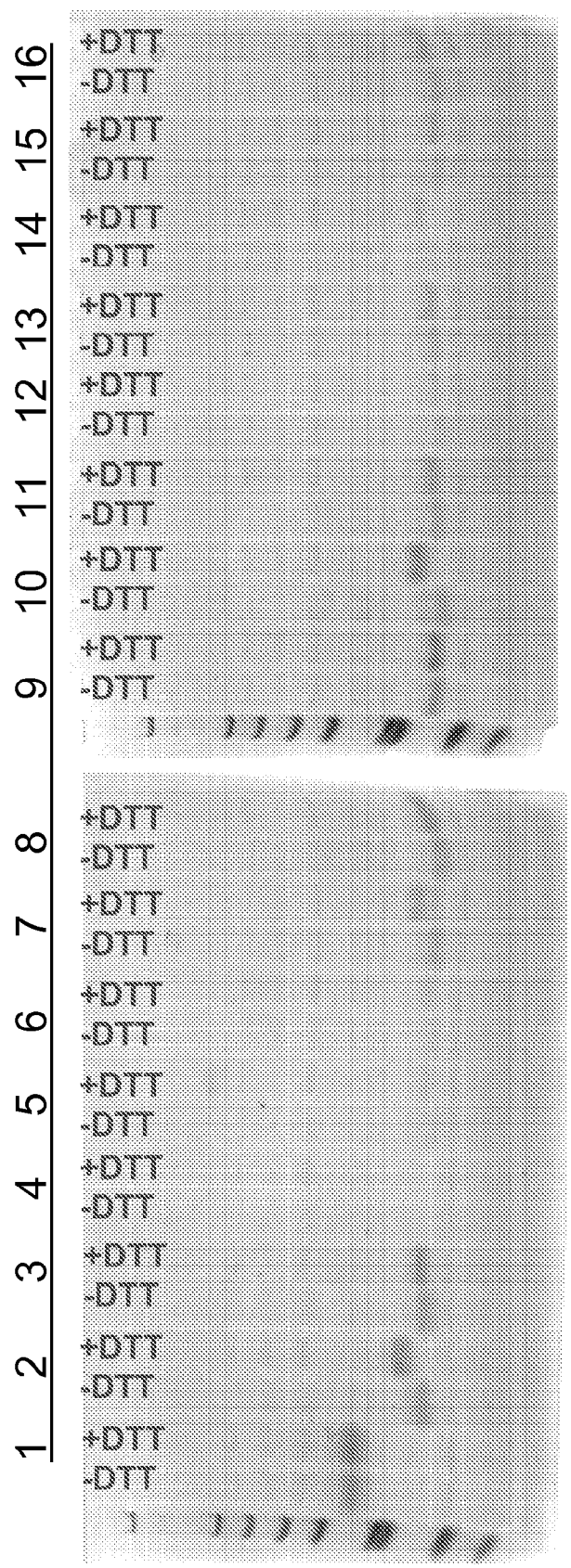
FIG. 5 illustrates an SDS-PAGE of polypeptides expressed from a thrombospondin domain scaffold library and isolated using heat lysis.

To demonstrate the generality of the heat-lysis production method, three degenerate libraries of domains based on the thrombospondin type 1, Trefoil/PD, and integrin beta protein domain scaffolds were created. Oligos comprising the conserved and variable positions in the consensus sequence for each family were synthesized and assembled using standard methods to create a library of full-length genes. Libraries representing each family were cloned separately into a pET24b-derivative plasmid under control of an inducible T7 promoter system. The libraries were then transformed into BL21 (DE3) Gold *E. coli*, and individual clones were picked randomly and grown in 96-well plates at 37° C. to an OD of ~1. Protein expression was induced by addition of IPTG to 1 mM, and cultures were further incubated at 37° C. for three hours. Cultures were harvested by centrifugation and cells were resuspended in 120 mM NaCl, 20 mM Tris pH 7.5, 1 mM CaCl$_2$. Cells were subjected to heat lysis by incubation at 95° C. for 10 minutes, cooled on ice, then clarified by centrifugation. Samples of the supernatant were then analyzed by SDS-PAGE in the presence or absence of dithiothreitol (DTT). FIGS. 3-5 show that expressed protein was substantially purified using the heat lysis technique for the majority of randomly chosen clones in each library. In addition, significant migration shifts upon addition of DTT were observed for clones based on the thrombospondin and integrin beta scaffolds, indicating that significant disulfide bond formation had occurred in these proteins.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing an isolated heat stable polypeptide capable of binding to a target molecule, said heat stable polypeptide comprising at least two LDL receptor A-domains, the method comprising,
    (a) culturing prokaryote cells that recombinantly express said heat stable polypeptide capable of binding to a target molecule;
    (b) heating the cells to between 50-100° C. by a continuous flow heating process for a time sufficient to lyse at least 50% of the cells;
    (c) incubating the resulting intact and lysed cells at a temperature of between −10° C. and 10° C.; and
    (d) separating the expressed heat stable polypeptides from the intact cells and lysed cells;
    wherein more than 80% of said separated, expressed, polypeptides are heat stable polypeptides that retain the ability to bind to said target molecule.

2. The method of claim 1, wherein the continuous flow heating process of step (b) comprises heating the cells to 65-95° C. for a time sufficient to lyse at least 50% of the cells.

3. The method of claim 1, wherein the heat stable polypeptide comprises at least three domains and wherein each domain comprises at least three disulfide bonds and is between 25-100 amino acids long.

4. The method of claim 1, wherein the heat stable polypeptide has no more than 6 domains.

5. The method of claim 1, wherein the heat stable polypeptide has no more than 100 amino acids.

6. The method of claim 1, wherein each LDL receptor A-domain comprises at least three disulfide bonds.

7. The method of claim 1, wherein said incubating step (c) is carried out for at least a minute.

8. The method of claim 1, wherein said incubating step (c) comprises cooling the cells to a temperature of less than 5° C. for at least a minute.

9. The method of claim 1 wherein said incubating step (c) comprises subjecting the cells to a decreasing temperature gradient.

10. The method of claim 9, wherein the temperature is decreased by at least 1 degree (Celsius) per minute, for at least 5 minutes.

11. The method of claim 1, wherein said continuous flow heating step (b) comprises passing the cells through a stainless steel coil.

12. The method of claim 1, wherein, said incubating step (c) comprises placing the prokaryotic cells in an ice bath.

13. The method of claim 11, wherein said incubating step (c) comprises passing the cells through a stainless steel coil in a cooling bath.

* * * * *